United States Patent [19]

Nadler

[11] Patent Number: 5,962,415
[45] Date of Patent: Oct. 5, 1999

[54] COMPOSITIONS COMPRISING A PEPTIDE INHIBITOR OF NUCLEAR PROTEIN TRANSLOCATION AND AN IMMUNOSUPPRESSANT AND METHODS OF USE THEREOF

[75] Inventor: Steven G. Nadler, Princeton, N.J.

[73] Assignee: Bristol-Myers Squibb Co., New York, N.Y.

[21] Appl. No.: 09/072,429

[22] Filed: May 4, 1998

Related U.S. Application Data

[63] Continuation-in-part of application No. 08/928,958, Sep. 12, 1997, Pat. No. 5,877,282
[60] Provisional application No. 60/026,978, Sep. 20, 1996.
[51] Int. Cl.⁶ .................................................. C07K 14/00
[52] U.S. Cl. .............................. 514/12; 514/2; 530/350; 530/300
[58] Field of Search .................. 514/12, 2; 530/350, 530/300

[56] References Cited

U.S. PATENT DOCUMENTS 5,877,282  3/1999  Nadler ..................................... 530/350

FOREIGN PATENT DOCUMENTS

WO 94/04696  3/1994  WIPO .
WO 95/34295  12/1995  WIPO .

OTHER PUBLICATIONS

Mukaigawa et al. (1991), Journal Virology 65:(1)253–254.
Perez et al. (1992) Journal of Cell Science 102:717–722.
Fulton et al. (Feb. 1996) Drug Evaluation 279–299.
Buelow et al. (1995) Transplantation 59:455.
Berlose et al. (1996) Eur. J. Biochem. 242:372–386.
Hinkes et al. (1993) Journal of Biological Chemistry 268:(15)11440–11448.
Imamura et al. (1992) Journal of Biological Chemistry 267:(8)5676–5679.
Kentrup et al. (1996) Journal of Biological Chemistry 271:(7)3488–3498.
Martin et al. (1991) Journal of Virology 232–244.
Journal of the American Society of Nephrology 7:1890.
Journal of Heart and Lung Transplantation vol. 14, No. 1, Part 2, Abstracts S51.

*Primary Examiner*—Karen Cochrane Carlson
*Attorney, Agent, or Firm*—Christopher A. Klein; Joseph M. Sorrentino

[57] ABSTRACT

Novel compositions of immunosuppressants, such as cyclosporin, and polypeptide inhibitors of cytoplasmic protein nuclear translocation are disclosed. The compositions have, in addition to at least one immunosuppressant, at least one polypeptide inhibitor of nuclear translocation that has a signal sequence and at least one, preferably two, nuclear localization sequences. The compositions are useful as immunosuppression, antiviral and antitumor agents, preferably to prevent rejection of transplanted organs or tissue.

17 Claims, 21 Drawing Sheets

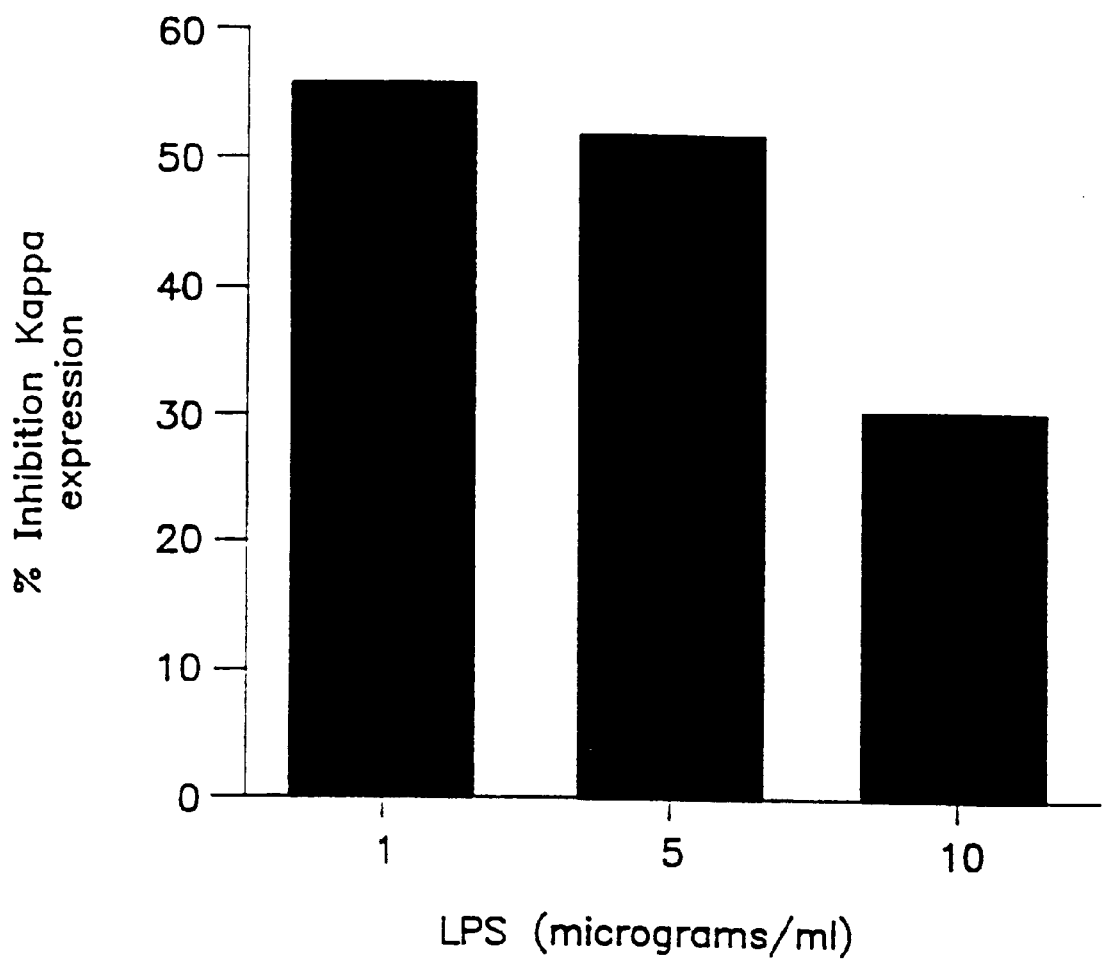
FIG. IC

SV40MEM peptide     NF-κBMEM peptide 0    1    0.1    10

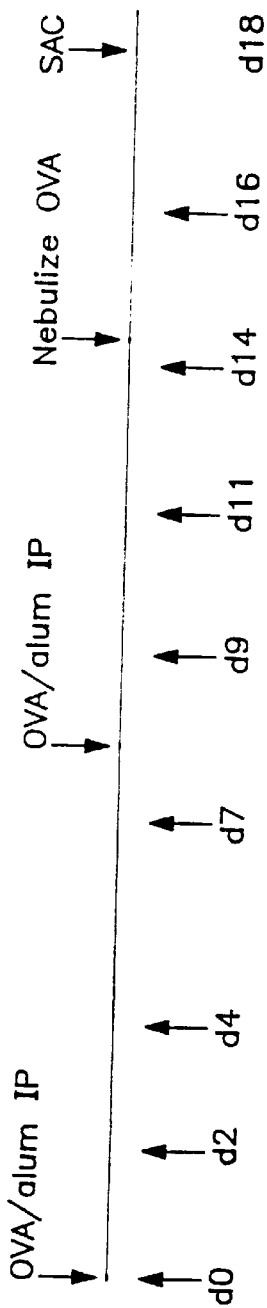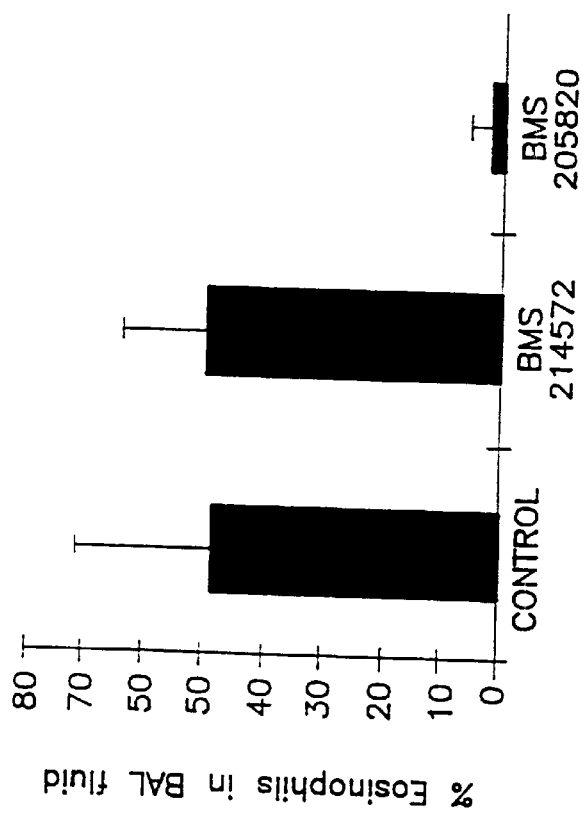
FIG. 15A
FIG. 15B

COMPOSITIONS COMPRISING A PEPTIDE INHIBITOR OF NUCLEAR PROTEIN TRANSLOCATION AND AN IMMUNOSUPPRESSANT AND METHODS OF USE THEREOF

CROSS-REFERENCE TO RELATED APPLICATION

This application is a continuation-in-part of U.S. Ser. No. 08/928,958 filed Sep. 12, 1997, now U.S Pat. 5,877,282, which is related to provisional patent application Ser. No. 60/026,978, filed Sept. 20, 1996, from which priority is claimed under 35 USC 1 19(e)(1). Both of the above-referenced applications are incorporated herein by reference in their entirety.

TECHNICAL FIELD

The present invention relates generally to immunotherapy using a combination of polypeptide inhibitors of gene expression and other immunosuppressants. More particularly, the invention relates to polypeptide inhibitors of nuclear protein translocation which have gene expression modulating activity, immunosuppressive activity, antiviral activity, and antitumor activity used in combination with immunosuppressants such as cyclosporin A.

BACKGROUND OF THE INVENTION

Nuclear transport is essential to a number of biological processes including gene expression and cell division, as well as to viral replication, tumorigenesis and tumor cell proliferation. The mechanism of nuclear transport has only recently been characterized in detail and has been shown to involve a number of discrete steps. Proteins that are destined to be transported into the nucleus contain within their amino acid sequence a short stretch of amino acids termed a nuclear localization sequence ("NLS"). These sequences are generally basic in nature, however, there has been no consensus sequence identified. Thus, there is a wide variety of these sequences that appear to be specific for particular proteins.

Within the cell, these NLSs may be either masked or unmasked by accessory proteins or by conformational changes within the NLS-containing protein. An NLS may be masked because it is buried in the core of the protein and not exposed on the surface of the protein. Unmasking of NLSs, and nuclear translocation of cytoplasmic proteins may be triggered by phosphorylation, dephosphorylation, proteolytic digestion, subunit association or dissociation of an inhibitory subunit, or the like. Accordingly, the masking and unmasking of NLSs provides a mechanism by which the transport of these cytoplasmic proteins into the nucleus may be regulated.

Nuclear translocation of transcription factors requires the presence of an unmasked or activated NLS in the nucleus-targeted protein. The binding of certain ligands to cell surface receptors activates the nuclear translocation of cytoplasmic transcription factors. Once in the nucleus, these transcription factors exert gene expression modulatory activity.

NF-κB is a ubiquitous transcription factor found in various levels and states of activation in different cell types. NF-κB is composed of several different subunits including p65, p50, c-rel p52 and p105. Recent studies suggest that distinct NF-κB complexes contribute to the regulatory control of gene transcription. The function and regulation of NF-κB has been most well-characterized in lymphocytic cells. In these cells, there is a wide variety of target genes, e.g., immunoregulatory genes, that are regulated by NF-κB including κ Ig light chains. Such genes include those that encode the interleukin-2" ("IL-2α") receptor, interleukin-2 ("IL-2"), interleukin-6 ("IL-6"), tumor necrosis factor-α ("TNF-α"), and the like.

In unstimulated cells, a major form of NF-κB is a heterodimer of p50 and p65 (RelA) subunits. Nonactive NF-κB is retained in the cytoplasm as an inactive complex by inhibitory proteins such as IκBα, β and γ. When cells are appropriately stimulated, e.g., by a proinflammatory stimulus such as a cytokine, the IκBs are degraded, thereby releasing free NF-κB dimers, which translocate to the nucleus and activate target genes, e.g., lymphokine genes and other immunoregulatory genes. This response is transient and is terminated through delayed NF-κB-mediated IκBα induction.

Recently it has been demonstrated that glucocorticoids exert their immunosuppressive activity by inhibiting NF-κB nuclear translocation. Scheinman et al. (1995) *Science* 270:283–286 and Auphan et al. (1995) *Science* 270:286–290 independently demonstrated that the inhibition is mediated by an increase in the induction by glucocorticoids of IκB inhibitory proteins. These investigators proposed that inhibitors of NF-κB may be useful immunosuppressive and anti-inflammatory agents. Such an NF-κB nuclear translocation inhibitor, comprising an NLS from the p50 subunit of NF-κB attached to a membrane-permeable polypeptide motif, was described in Lin et al. (1995) *J Biol. Chem.* 270:14255–14258.

Nuclear translocation of proteins other than endogenous transcription factors and other cytoplasmic proteins also depends on the presence of an activated or unmasked NLS. For example, nuclear translocation of the retroviral preintegration complex is a crucial step in human immunodeficiency virus type-1 ("HIV-1") replication in nondividing cells such as monocytes and growth-arrested T cells. Such translocation is dependent on the presence of an NLS in the N-terminal portion of HIV matrix antigen ("MA") p 17. Indeed, the HIV-1 enhancer contains tandem binding sites for NF-κB that can be essential for virus replication (Ross et al. (I 991) *J Virol.* 65:4350–4358; Parrott et al. (1991) *J Virol* 65:1414–1419). Nuclear translocation of the HIV-1 preintegration complex can be partially inhibited by an excess of the SV40 large T antigen NLS (Gulizia et al. (1994) *J Virol.* 68:2021–2025). Furthermore, Dubrovsky et al. (1995) *Molecular Med.* 2:217–230 reported that a series of compounds capable of binding to and reacting with the HIV-1 MA p17 NLS inhibit HIV-1 replication in human monocytes.

In addition, tumorigenesis and tumor cell proliferation are regulated by the expression of oncoproteins, many of which are cytoplasmic transcription factors that are translocated into the nucleus by virtue of the presence of an NLS. Miller et al. (1996) *J Cell Biochemistry* 60:560.

Prior to Applicants invention, those in the art failed to demonstrate the synergism between peptide inhibitors of nuclear translocation and other imunosuppressants, such as cyclosporin. Buelow et al. (1995) *Transplantation* 59:455 demonstrated that therapy with a small synthetic peptide derived from the α1 helix of an HLA class I molecule (called the ALLOTRAP peptide), combined with a subtherapeutic dose of cyclosporin, led to the prolonged survival of allografts. The ALLOTRAP peptide, however, does not inhibit nuclear translocation of protein, an essential element of Applicants invention.

Many immunosuppressants are known in the art to be useful in treating autoimmune disease and in preventing transplant rejection. Examples of known immunosuppressants useful in compositions of the present invention are cyclosporin A, mycophenolate mofetil, rapamycin, FK506, and steroids. Compositions of the present invention comprising at least one peptide inhibitor of nuclear translocation of a protein also comprise at least one immunosuppressant. Together, the peptide inhibitor and immunosuppressant work synergistically to provide better immune suppression than either treatment alone.

Accordingly, inhibitors of nuclear translocation of cytoplasmic proteins would be useful as gene expression modulating agents, immunoregulatory agents, antiviral agents, antitumor agents, and the like. Such inhibitors, in combination with other immunosuppressant compounds such as cyclosporin A, would provide useful compositions to regulate immune responses (e.g., prevent transplant rejection).

SUMMARY OF THE INVENTION

The present invention provides for compositions comprising at least one immunosuppressant and a polypeptide that can be introduced into an intact cell for the purpose of inhibiting the nuclear translocation of a cytoplasmic protein. The polypeptide contains at least one, more preferably two, NLSs and an amino acid sequence that can deliver the polypeptide through the cytoplasmic membrane into the cell. The inventors herein have found that such a composition exhibits surprisingly superior immunosuppressive characteristics compared to using an immunosuppressant or polypeptide alone.

Accordingly, in one embodiment, the composition of the present invention comprises a polypeptide comprising a signal sequence peptide and at least one NLS covalently attached thereto.

In another embodiment, the invention is directed to a method of suppressing an immune response of a subject comprising administering to the subject an immunosuppressive amount of a composition comprising a polypeptide comprising a signal sequence peptide and at least one NLS and an immunosuppressant. In a preferred embodiment, the immunosuppressant is cyclosporin A.

In a further embodiment, the invention is directed to a method of treating or preventing a viral infection in an individual comprising administering to the individual an effective antiviral amount of a composition comprising a polypeptide inhibitor of nuclear translocation of a cellular protein, said inhibitor comprising a signal sequence peptide and at least one NLS, and an immunosuppressant.

In yet a further embodiment, the invention is directed to a method of preventing transplant rejection in a subject comprising administering to the subject a composition comprising an immunosuppressant and a polypeptide inhibitor of nuclear translocation, wherein the polypeptide comprises a signal sequence peptide and at least one NLS. In a preferred embodiment the immunosuppressant is cyclosporin A.

These and other embodiments of the subject invention will readily occur to those of ordinary skill in the art in view of the disclosure herein.

BRIEF DESCRIPTION OF THE FIGURES

FIG. 1C is a graphical representation of the effect of increasing LPS concentrations on SV40MEM-inhibited κ Ig light chain production in 70Z/3 murine leukemia pre-B cells.

FIG. 15A is a time line depicting the administration scheme for the intraperitoneal injection of ovalbumin (OVA), nebulized OVA, BMS-205820 and C-MYCMEM.

FIG. 15B shows the % eosinophils in lung following the treatment outlined in FIG. 15A.

DETAILED DESCRIPTION

Figure 1A:
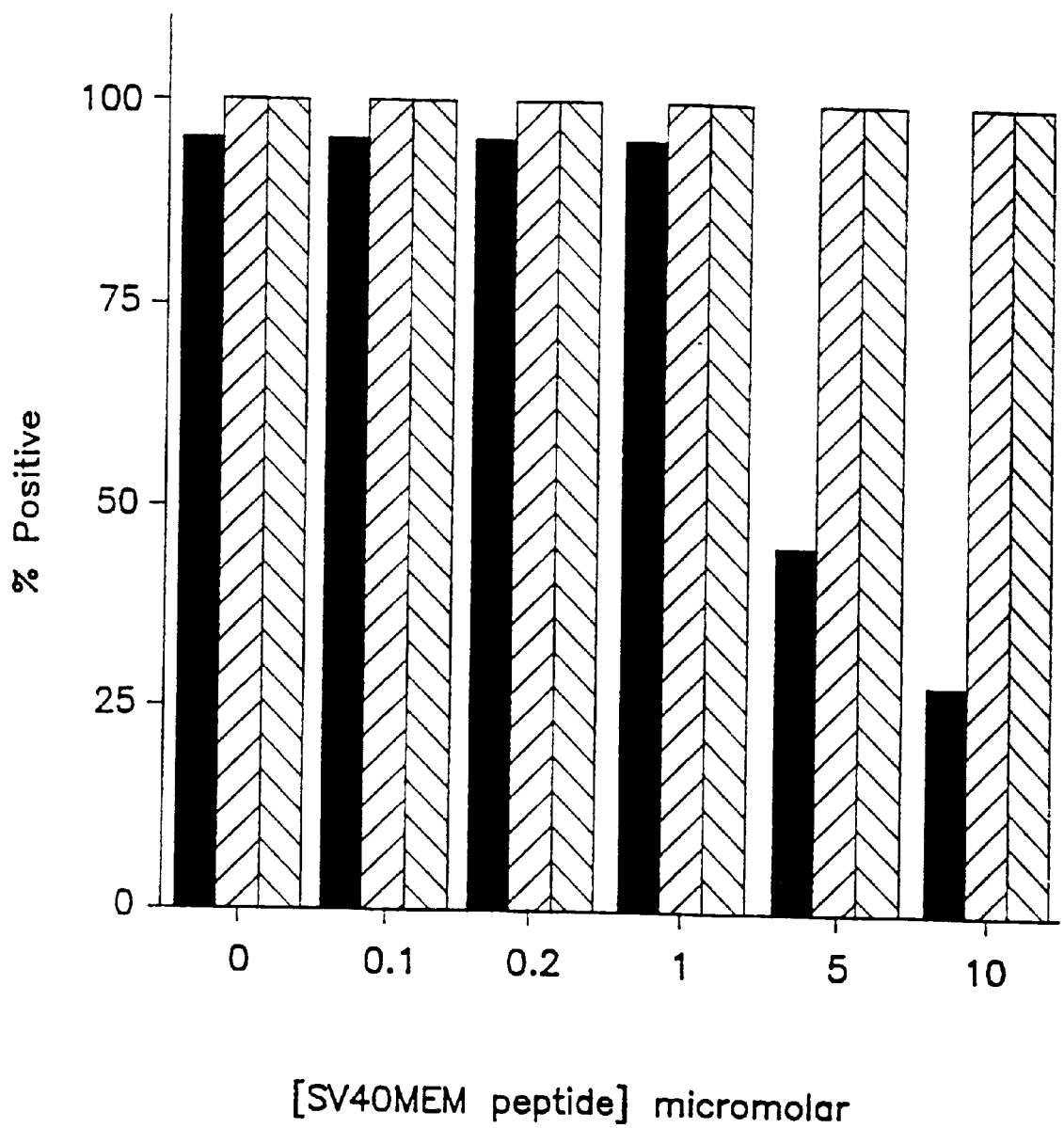
FIG. 1A is a graphical representation of the effect of PKKKRKVAAVALLPAVLLALLAPKKKRKVC (SEQ ID NO:1) (the "SV40MEM" polypeptide) on lipopolysaccharide ("LPS")-stimulated surface antigen expression in 70Z/3 murine leukemia pre-B cells (solid bar: κ Ig light chain; stippled bar: IL-2α receptor; striped bar: CD45).

The practice of the present invention will employ, unless otherwise indicated, conventional techniques of protein chemistry and biochemistry, molecular biology, microbiology and recombinant DNA technology, which are within the skill of the art. Such techniques are explained fully in the literature. See, e.g., Sambrook, Fritsch & Maniatis, *Molecular Cloning. A Laboratory Manual,* Second Edition (1989); *DNA Cloning,* Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

As used herein, the term "signal sequence" or "signal sequence peptide" is used to indicate a peptide that is capable of directing the movement of the polypeptide of which it is a part through a cell membrane. In particular, the term is used to indicate a peptide that directs the movement of a polypeptide across the cytoplasmic membrane into the cell. The term "signal sequence" is intended to encompass not only the signal sequence of a particular polypeptide, but also fragments or derivatives thereof that are capable of delivering a polypeptide through a cell membrane. A "signal sequence" may be composed of L- or D-amino acids, preferably D-amino acids.

The terms "nuclear localization sequence" and "NLS" are used interchangeably to indicate a peptide that directs the transport of a protein with which it is associated from the cytoplasm of a cell across the nuclear envelope barrier. The term "NLS" is intended to encompass not only the nuclear localization sequence of a particular peptide, but also derivatives thereof that are capable of directing translocation of a cytoplasmic polypeptide across the nuclear envelope barrier. NLSs are capable of directing nuclear translocation of a polypeptide when attached to the N-terminus, the C-terminus, or both the N- and C- termini of the polypeptide. In addition, a polypeptide having an NLS coupled by its N- or C-terminus to amino acid side chains located randomly along the amino acid sequence of the polypeptide will be translocated. Adam et al. (1990) *J Cell. Biol.* 111:807–818. "Nuclear localization sequences" may be composed of D- or L-amino acids.

By "interchangeably flanked at its amino- and carboxy-termini by a first and a second NLS" is intended to mean that the first or second NLS may be located at either the amino- or carboxy-terminus of the signal sequence polypeptide.

An "inhibitor of nuclear translocation" is a polypeptide composed of a signal sequence peptide and at least two NLSs which inhibits, e.g., either decreases or halts, nuclear localization of a cytoplasmic protein. Preferably, the polypeptide comprises a signal sequence peptide interchangeably flanked at its amino- and carboxy-termini by a first and a second NLS. The NLSs at the N- and C-termini may be the same or different. In one preferred embodiment, the signal sequence peptide and the NLSs are each composed of L-amino acids. In another preferred embodiment, the signal sequence peptide and the NLSs are each composed of D-amino acids.

A "derivative" of a polypeptide is intended to include homologous polypeptides in which conservative amino acid substitutions have been made, as well as to include other amino acid substitutions that result in a polypeptide that retains its function, e.g., as a signal sequence peptide, an NLS, or an inhibitor of nuclear localization. A "derivative" of a peptide may be a peptide mimetic.

"Peptide mimetics" are structures which serve as substitutes for peptides in interactions with acceptor molecules (see Morgan et al. (1989) *Ann. Reports Med. Chem.* 24:243–252 for a review of peptide mimetics). Peptide mimetics, as used herein, include synthetic structures which may or may not contain amino acids and/or peptide bonds, but retain the structural and functional features of a peptide ligand. The term, "peptide mimetics" also includes peptoids and oligopeptoids, which are peptides or oligomers of N-substituted amino acids (Simon et al. (1972) *Proc. Natl. Acad. Sci. USA* 89:9367–9371). Further included as peptide mimetics are peptide libraries, which are collections of peptides designed to be of a given amino acid length and representing all conceivable sequences of amino acids corresponding thereto. Methods for the production of peptide mimetics are described more fully below.

Two polypeptide sequences are "substantially homologous" when at least about 85% (preferably at least about 85% to 90%, and most preferably at least about 95%) of the nucleotides or amino acids match over a defined length of the molecule. As used herein, substantially homologous also refers to sequences showing identity to the specified polypeptide sequence.

The terms "polypeptide", "peptide" and "protein" are used interchangeably and refer to any polymer of amino acids (dipeptide or greater) linked through peptide bonds. Thus, the terms "polypeptide", "peptide" and "protein" include oligopeptides, protein fragments, analogues, muteins, fusion proteins and the like.

The following single-letter amino acid abbreviations are used throughout the text:

| Alanine | A | Arginine | R |
|---|---|---|---|
| Asparagine | N | Aspartic acid | D |
| Cysteine | C | Glutamine | Q |
| Glutamic acid | E | Glycine | G |
| Histamine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

By an "isolated polypeptide" is meant a polypeptide which is devoid of, in whole or part, tissue or cellular components with which the protein is normally associated in nature. Thus, a polypeptide contained in a tissue extract would constitute an "isolated" polypeptide, as would a polypeptide synthetically or recombinantly produced.

By "mammalian subject" is meant any member of the class Mammalia, including, without limitation, humans and non-human primates, such as chimpanzees and other apes and monkey species; farm animals such as cattle, sheep, pigs, goats and horses; domestic mammals such as dogs and cats; and laboratory animals including rodents such as mice, rats and guinea pigs. The term does not denote a particular age. Thus, adult, newborn and fetal mammals are intended to be covered.

The term "treatment" as used herein refers to either (i) the prevention of infection or reinfection (prophylaxis), or (ii) the reduction or elimination of symptoms of the disease of interest (therapy).

The term "immunosuppressant" is used to refer to any compound that is known or found to suppress or prevent an undesired immune response, e.g., prevent the immune system's rejection of a transplanted organ. Examples of "immunosuppressants" include, but are not limited to, cyclosporin A, mycophenolate mofetil, rapamycin, FK506, steroids, and any other known immunosuppressant compound. One or more immunosuppressants may be used in a composition of the present invention.

The term "composition" when used herein refers to a composition comprising a polypeptide inhibitor of nuclear translocation and an immunosuppressant.

By "immunosuppressive amount" is meant an amount of a composition of the present invention sufficient to stop or suppress an undesired immune response (e.g., stop or slow progression of an autoimmune disease) or prevent an immune response from occurring (e.g., prevent immune rejection of a transplanted tissue or organ). The exact amount of a composition of the present invention that is immunosuppressive can be determined by one skilled in the art, and depends upon such factors as target indication, a subject's age, weight and health, and mode of delivery.

B. General Methods

Central to the present invention is the discovery that compositions comprising at least one immunosuppressant in combination with at least one polypeptide molecule that inhibits nuclear localization of cytoplasmic proteins are more effective at modulating an immune response than either the immunosuppressant or polypeptide alone. The polypeptide molecules comprise a signal sequence peptide and at least on e NLS. The polypeptide inhibitors, and derivatives thereof, provide useful tools for introducing an exogenous polypeptide comprising an NLS into an intact cell to inhibit nuclear translocation of a cellular protein, for studying the role of nuclear translocation in the regulation of cellular processes.

Since the nuclear translocation of certain cellular peptides is required for the host organism to mount an immune response, the polypeptide inhibitors in combination with other immunosuppressants are useful as immunosuppression compositions. Immune responses are typically manifested by the expression of antibodies, the production of a number of cytokines, and/or the expression of cell surface receptors. Thus, inhibition of immune responses by the compositions of the present invention can take the form of: inhibition of antibody production, including the production of antibody component peptides such as a κ light chain polypeptide; inhibition of cytokine production, including such cytokines as interleukin-1, interleukin-2, interleukin-4, interleukin-6, interleukin-10, tumor necrosis factor, or granulocyte-macrophage colony-stimulating factor; and/or the inhibition of the expression of cell-surface receptors such as an interleukin-2 receptor, gp39, CD40, CD45, CD80, CD86, ICAM, ELAM, major histocompatibility complex (“MHC”) class II, or VCAM. Clark et al. (1994) *Nature* 367:425.

By virtue of their superior immunosuppressive activities, the compositions of the present invention, comprising at least one polypeptide inhibitor and at least one additional immunosuppressive agent, are useful in the treatment of a wide variety of immune disorders, including but not limited to, the treatment of autoimmune diseases such as rheumatoid arthritis, multiple sclerosis, juvenile-onset diabetes, systemic lupus erythematosus (SLE), autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, and autoimmune thrombocytopenic purpura (see e.g., Paul, W. E. (1993) *Fundamental Immunology,* Third Edition, Raven Press, New York, Chapter 30, pp. 1033–1097; and Cohen et al. (1994) *Autoimmune Disease Models, A Guidebook,* Academic Press, 1994), as well as to prevent the rejection of transplanted tissue or organs.

Similarly, the compositions of the present invention are useful for treating physical symptoms manifested by responses to allergens which can initiate a state of hypersensitivity, or which can provoke a hypersensitivity reaction in a subject already sensitized with the allergen. Such physical symptoms include asthma, joint swelling, urticaria, and the like. Additionally, due to the superior immunosuppressive properties, the compositions of the present invention are useful in the treatment of sepsis and in the prevention of septic shock, a potentially lethal condition caused by the uncontrolled production of certain cytokines due to the presence of endotoxins, such as lipopolysaccharide (LPS), from extracellular bacteria.

Furthermore, since many viruses, e.g., herpes virus, cytomegalovirus, retroviruses, and the like, make use of the host cell's nuclear translocation machinery, the compositions of the present invention comprising inhibitory polypeptides are useful as antiviral agents. In addition, since tumorigenesis and tumor cell proliferation appear to be mediated by the expression of oncogenes to make oncoproteins, many of which are transcription factors that are translocated into the nucleus, Miller et al. (1996), supra, the compositions of the present invention comprising polypeptide inhibitors, or derivatives thereof, can be used to suppress tumor growth.

Polypeptide inhibitors useful in the compositions of the present invention include sequences of amino acids that comprise signal sequences from such polypeptides as the antennapedia homeodomain, FGF, HIV Tat, or Hsc70, and derivatives or mimetics thereof capable of delivering the inhibitor through the cytoplasmic membrane into the cell. Preferred signal sequences include RQIKIWFQNRRMK-WKK (SEQ ID NO:7), AAVALLPAVLLALLA (SEQ ID NO:8), AAVALLPAVLLALLAP (SEQ ID NO:4), CFIT-KALGISYGRKKRRQRRRPPQGSQTH (SEQ ID NO:9), and the like, or derivatives or mimetics thereof capable of delivering the inhibitor through the cytoplasmic membrane into the cell.

Candidate signal sequences can be tested for their ability to direct the translocation of proteins across cell membranes, for example, by monitoring the localization of exogenous detectably labeled proteins into the cell cytoplasm. Lin et al. (1995), supra, describe the use of radiolabeled proteins. In vitro nuclear peptide import can be measured using NLS peptides coupled to a fluorescent protein by methods described in Adam et al. (1990), supra.

Polypeptide inhibitor useful in compositions of the present invention further comprise at least one NLS, more preferably at least two NLSs. The NLSs can be covalently bonded to the N-terminus, to the C-terminus, to both the N- and C-termini of the signal sequence polypeptide, to amino acid side chains located along the amino acid sequence of the signal sequence polypeptide, or any combination thereof. Preferably, the signal sequence polypeptide is interchangeably flanked at its aminoand carboxy-termini by a first and a second NLS. If at least two NLSs are present, first and second NLSs may be the same or different. A discussion of NLSs and a list of NLSs can be found in Boulikas (1993) *Crit. Rev. Eukaryotic Gene Expression* 3:193–227, and references cited therein.

Approaches for identifying NLSs include: (1) gene fusion experiments between a candidate NLS-coding DNA segment and the gene coding for a cytoplasmic protein (see, e.g., Silver et al. (1984) *Proc. Natl. Acad. Sci. U.S.A.* 81:5951; Moreland et al. (1987) *Mol. Cell. Biol.* 7:4048; and Picard et al. (1987) *EMBO J* 6:3333); (2) nuclear import of nonnuclear proteins conjugated to synthetic NLS peptides (see, e.g., Goldfarb et al. (1986) *Nature* 322:641; Markland et al. (1987) *Mol Cell. Biol* 7:4255; and Chelsky et al. (1989) *Mol. Cell. Biol.* 9:2487); and (3) site-directed mutagenesis of a specific segment of a nuclear protein, resulting in its cytoplasmic retention (see, e.g., Greenspan et al. (1988) *J Virol.* 62:3020; van Etten et al. (1989) *Cell* 58:669; and Boulukos et al. (1989) *Mol. Cell. Biol.*9:5718).

Preferred NLSs include PKKKRKV (SEQ ID NO: 10) and KKKRKVC (SEQ ID NO:1 1) from the SV40 large T antigen (see, Kalderon et al. (1984) *Cell* 39:499), GKKRSKA (SEQ ID NO: 12) from yeast histone H2B (see, Moreland et al. (1987) *Mol. Cell. Biol.* 7:4048), KRPRP (SEQ ID NO:13) from adenovirus EIA (see, Lyons et al. (1987) *Mol. Cell. Biol.* 7:2451), GNKAKRQRST (SEQ ID NO:14) from the v-rel oncogene of the avian reticuloendotheliosis retrovirus strain T (see, Gilmore et al. (1988) *J Virol.* 62:703), GGAAKRVKLD (SEQ ID NO:15) from the human c-myc oncoprotein (see, Chelsky et al. (1989) *Mol. Cell. Biol.* 9:2487), SALIKKKKKMAP (SEQ ID NO:16) from the murine c-abl (IV) gene product (see, Van Etten et al. (1989) *Cell* 58:669), RKLKKLGN (SEQ ID NO:17) from the human or rat androgen receptor (see, Guiochon-Mantel et al. (1989) *Cell* 57:1147), PQPKKKP (SEQ ID NO:18) from protein p53 (see, Dang et al. (1989) *J Biol. Chem.* 264:18019)), ASKSRKRKL (SEQ ID NO:19) from viral Jun, a transcription factor of the AP-1 complex (see, Chida et al. (1992) *Proc. Natl. Acad. Sci. USA* 89:4290), KKKYK (SEQ ID NO:20) and KKKYKC (SEQ ID NO:21), both of which are from the human immunodeficiency virus matrix protein (see, Bukrinsky et al. (1993) *Nature* 365:666), KSKKK (SEQ ID NO:22) from the human immunodeficiency virus matrix 2 protein (see, Bukrinsky et al. (1993), supra), AKRVKL (SEQ ID NO:6) and KRVKLC (SEQ ID NO:23) both of which are from the human c-myc oncoprotein (see, Chelsky et al. (1989), supra), and derivatives and mimetics thereof that are effective as an NLS.

Polypeptide inhibitors useful in compositions of the present invention may be synthesized by conventional techniques known in the art, for example, by chemical synthesis such as solid phase peptide synthesis. Such methods are known to those skilled in the art. In general, these methods employ either solid or solution phase synthesis methods, well known in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptide: Analysis Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups and any solid support are removed either sequentially or concurrently to afford the final polypeptide. By simple modification of this general procedure, it is possible to add more than one amino acid at a time to a growing chain, for example, by coupling (under condition that do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc), benxyloxycarbonyl (Cbz), p-toluenesulfonyl (Tos); 2,4-dinitrophenyl, benzyl (Bzl), biphenylisopropyloxycarboxycarbonyl, cyclohexyl, isopropyl, acetyl, o-nitrophenylsulfonyl, and the like. Of these, Boc and Fmoc are preferred.

Typical solid supports are generally cross-linked polymeric materials. These include divinylbenzene cross-linked styrene-based polymers, for example, divinylbenzene-hydroxymethylstyrene copolymers, divinylbenzene-chloromethylstyrene copolymers, and divinylbenzene-benzhydrylaminopolystyrene copolymers. The divinylbenzene-benzhydrylaminopolystyrene copolymers, as illustrated herein using p-methyl-benzhydrylamine resin, offers the advantage of directly introducing a terminal amide functional group into the peptide chain, which function is retained by the chain when the chain is cleaved from the support.

In one preferred method, the polypeptides are prepared by conventional solid phase chemical synthesis on, for example, an Applied Biosystems, Inc. (ABI) 430A peptide synthesizer using a resin that permits the synthesis of the amide peptide form and using t-Boc amino acid derivatives (Peninsula Laboratories, Inc.) with standard solvents and reagents. Polypeptides containing either L- or D-amino acids may be synthesized in this manner. Polypeptide composition is confirmed by quantitative amino acid analysis and the specific sequence of each peptide may be determined by sequence analysis.

Alternatively, inhibitor polypeptides useful in compositions of the present invention can be produced by recombinant DNA techniques by synthesizing DNA encoding the desired polypeptide, along with an ATG initiation codon. Once coding sequences for the desired polypeptides have been synthesized or isolated, they can be cloned into any suitable vector for expression. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV 1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp 19 (Saccharomyces) and bovine papilloma virus (mammalian cells). See, generally, *DNA Cloning:* Vols. I & II, supra; Sambrook et al., supra; B. Perbal, supra. Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. Heterologous leader sequences can be added to the coding sequence which cause the secretion of the expressed polypeptide from the host organism. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the polypeptide of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning,* Vols. I and II, supra; *Nucleic Acid Hybridization,* supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis,* and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda,* and Trichoplusia ni. The proteins may also be expressed in Trypanosomes.

Depending on the expression system and host selected, the peptides useful in compositions of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art. Once purified, the amino acid sequences of the proteins can be determined, i.e., by repetitive cycles of Edman degradation, followed by amino acid analysis by HPLC. Other methods of amino acid sequencing are also known in the art.

As explained above, peptide mimetics which structurally and functionally mimic the peptide inhibitors described above will also find use herein and may be generated using the following strategies and procedures. Generally, mimetics are designed based on information obtained by systematic replacement of L-amino acids by D-amino acids or, in the case of a polypeptide inhibitor that is made of D-amino acids, the systematic replacement of D-amino acids by L-amino acids, replacement of side chain moieties by a methyl group or pseudoisosteric groups with different electronic properties (see Hruby et al. (1990) *Biochem. J* 268:249–262), and by systematic replacement of peptide bonds in the above described polypeptide inhibitors with amide bond replacements. For example, analogues containing amide bond surrogates may be used to investigate aspects of peptide structure and function, such as rotational freedom in the backbone, intra- and intermolecular hydrogen-bond patterns, modifications of local and total polarity and hydrophobicity, and oral bioavailability.

Local conformational constraints can also be introduced to determine conformational requirements for activity of a candidate polypeptide mimetic inhibitor of nuclear translocation. For example, β,β-disubstituted amino acids may be used to examine the effects of conformational constraints on peptide activity (see, e.g., Manning et al. (1982) *J Med. Chem.* 25:408–414; Mosberg et al. (1983) *Proc. Natl. Acad. Sci. USA* 106:506–512; Pelton et al. (1985) *Proc. Natl. Acad. Sci. USA* 82:236–239).

The mimetics can include isosteric amide bonds such as Ψ[CH$_2$S], Ψ[CH$_2$NH], Ψ[CSNH$_2$], Ψ[NHCO], Ψ[COCH$_2$] and Ψ[(E) or (Z) CH=CH] (see, for review, Spatola (1983) in "Chemistry and Biochemistry of Amino Acids, Peptides and Proteins," Volume VII, (Weinstein, ed.), Marcel Dekker, New York, 267–357). Structures which mimic the tetrahedral transition state associated with hydrolysis of a substrate bond can also be present and include hydroxymethylene, fluoroketone moieties and phosphoramidate transition state mimics (Buhlmayer et al. (1988) *J Med. Chem.* 31:1839; Sham et al. (1988) *FEBS Lett.* 220:299; Matthews (1988) *Acc. Chem. Res.* 21:333). Cyclic amino acid analogues may be used to constrain amino acid residues to particular conformational states, e.g., αα'- and ββ'-substituted cyclic amino acids such as 1-aminocyclopentanecarboxylic acid (cycloleucine) and, ββ-cyclopentamethylene-β-mercaptopropionic acid (see Hruby et al. (1990), supra).

The mimetics can also include mimics of inhibitor peptide secondary structure—structures which can model the 3-dimensional orientation of amino acid residues into the known secondary conformations of proteins—including β-turn mimetics, such as phenoxathin ring system, and β-sheet mimics, such as epindolidione structures. Design, synthesis and conformational analysis of an α-helix inducing template has been described (Kemp et al.(1988) *Tetrahedron Lett.* 29:4931; Kemp et al. (1988) *Tetrahedron Lett.* 29:4935).

Similarly, peptoids will find use in the compositions described herein. Peptoids are oligomers of N-substituted amino acids (Simon et al. (1972), supra), and can be used as motifs for the generation of chemically diverse libraries of novel molecules, which can then be tested for nuclear translocation inhibitory activity. The monomers may incorporate t-butyl-based side-chain and 9-fluorenylmethoxycarbonyl (α-amine protection. Oligomerization of the peptoid monomers may be performed by, for example, in situ activation by either benzotriazol-1-yloxytris(pyrrolidino) phosphonium hexafluorphosphate or bromotris(pyrrolidino) phosphonium hexafluorophosphate. Other steps are identical to conventional peptide synthesis using α-(9-fluorenylmethoxycarbonyl)amino acids. Oligopeptoids may be identified which have activities comparable to the corresponding inhibitory polypeptides and, thus, are useful as inhibitors of nuclear translocation (see Simon et al. (1992), supra).

Peptide ligands that exhibit nuclear translocation inhibitory activity can be developed by using a biological expression system (see Christian et al. (1992) *J Mol. Biol.* 227:711–8; Devlin et al. (1990) *Science* 249:404–406; Cwirla et al. (1990) *Proc. Natl. Acad. Sci. USA* 87:6378–6382). The use of such systems allows the production of large libraries of random peptide sequences and the screening of these libraries for peptide sequences that have desired biochemical activity. The libraries may be produced by cloning synthetic DNA that encodes random peptide sequences into *Escherichia coli* expression vectors. In the filamentous phage system, foreign peptide sequences can be expressed on the surface of the infectious phage (see Smith (1985) *Science* 228:1315–1317; Parmley et al. (1988) *Gene* 73:305–318).

For example, a library may be made by ligating into an appropriate phage, a synthetic DNA fragment containing a degenerate coding sequence (NNK)$_n$, where N stands for an equal mixture of the deoxynucleotides G, A, T, and C, K stands for an equimolar mixture of G and T, and n stands for the number of amino acid residues desired in the product peptide. Phage are screened for expression of inhibitory activity. Those that express inhibitory activity can be cloned and propagated, their DNAs sequenced to determine the amino acid sequences of their expressed polypeptide which can be assessed for their ability to inhibit nuclear translocation.

Large libraries of polypeptide inhibitors can also be constructed by concurrent synthesis of overlapping peptides as described in U.S. Pat. No. 4,708,871 to Geysen. The solid support is generally a polyethylene or polypropylene rod onto which is graft polymerized a vinyl monomer containing at least one functional group to produce polymeric chains on the carrier. The functional groups are reacted to provide primary or secondary amine groups which are sequentially reacted with amino acid residues in the appropriate order to build the desired synthetic peptide using conventional methods of solid phase peptide chemistry.

Once synthesized or otherwise produced, the inhibitory activity of a candidate polypeptide or polypeptide mimetic can be tested by assessing the ability of the candidate to inhibit the lipopolysaccharide-induced nuclear translocation of NF-κB by, for example, using murine endothelial cells by the method described in Lin et al. (1995), supra.

In addition to one or more inhibitory polypeptides, the compositions of the present invention also comprise one or more immunosuppressants. Any known immunosuppressant, for example but not limited to, steroids, mycophenolate mofetil (See, Barry et al. (1996) *Drugs* 51(2):278–298), rapamycin, FK506, and/or cyclosporin may be used. Preferably, compositions of the present invention comprise cyclosporin alone or in combination with another inmmunosuppressant.

Cyclosporin (See, Faulds et al. (1993) *Drugs* 45(6) :953–1040) is a lipophilic cyclic polypeptide with unique immunosuppressive properties. It acts specifically and reversibly on lymphocytes (in particular T helper cells), producing selective suppression of cell-mediated immunity. This suppression is contingent on the mode of activation and is calcium-dependent.

Cyclosporin forms a complex with cyclophilin in the cytoplasm, which then binds to calcineurin, a calcium- and calmodulin-dependent phosphatase, in a calcium-dependent manner. Inhibition of calcineurin activity is implicated in the activation and/or translocation of a nuclear factor which binds to the interleukin-2 enhancer allowing the interleukin-2 gene to be transcribed. The transcription of several other cytokines, including interferon-γ, and several other interleukins, is also inhibited by cyclosporin.

Interleukin-2 production by T helper cells is a pivotal step in the evolution of the immune response. It is required for the activation and clonal expansion of T helper and T cytotoxic cells and the maturation of various other cell types. Thus, inhibition of interleukin-2 expression by cyclosporin reduces the production of a wide range of other cytokines, producing indirect effects on other cells involved in the immune response.

Applicants are the first to describe the use of compositions comprising peptide inhibitors of nuclear translocation, preferably peptides that inhibit the nuclear translocation of Nf-κB, and immunosuppressants such as cyclosporin to provide superior immunosuppression. The compositions of the present invention are useful in treating a wide range of immune disorders (evident to those skilled in the art) and, preferably, to prevent rejection of transplanted tissue or organs.

The present invention demonstrates that the combination of immunosuppressant(s), such as cyclosporin, and inhibitory polypeptides can be used in pharmaceutical compositions to treat autoimmune diseases and viral infections, or to suppress transplant rejection. In addition, the compositions can be administered to cancerous tissues in order to suppress tumor growth. The compositions of the present invention can be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular indication targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., *Remington's Pharmaceutical Sciences*, Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration to a tumor in question, or to a site of inflammation, e.g., direct injection into an arthritic joint, will also find use with the present invention.

Therapeutically effective doses will be easily determined by one of skill in the art and will depend on the severity and course of the disease, the patient's health and response to treatment, and the judgment of the treating physician.

The present invention encompasses treatment of a subject wherein an inhibitory peptide and an immunosuppressant are administered simultaneously or sequentially. Either simultaneous or sequential administration of an inhibitory peptide and an immunosuppressant fall within the scope of the present invention, which relates generally to immunotherapy using a combination of polypeptide inhibitors of gene expression, preferably polypeptide inhibitors of nuclear protein translocation, and other immunosuppressants such as cyclosporin A.

For example, the present invention contemplates simultaneous or sequential administration of at least one inhibitory polypeptide (e.g., the sequence as shown in SEQ ID NO:24) and at least one immunosuppressant (e.g., cyclosporin A) in a peptide:immunosuppressant ratio (on a mg/kg basis) of between 1:50 and 1:1, more preferably in a ratio of between 1:10 and 1:2. A composition of the present invention comprising the immunosuppressant cyclosporin A ("CsA"), for example, would preferably provide about 0.1–12.0 mg/kg/day of CsA, more preferably about 0.5–6.0 mg/kg/day, and more preferably about 1.0–3.0 mg/kg/day. Appropriate concentrations of inhibitory polypeptide in compositions of the present invention would be readily apparent by one skilled in the art following routine experimentation.

C. Experimental

Below are examples of specific embodiments for carrying out the present invention, e.g., selecting inhibitory polypeptides useful in compositions of the present invention and testing combinations of inhibitory polypeptides and immunosuppressants for immunosuppression activity. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Experimental Methods

Peptide Preparation

In general, polypeptides can be synthesized using a stepwise solid-phase synthesis method and purified on a $C_{18}$ reverse phase high performance liquid chromatography on a reverse-phase column eluted with a linear gradient of 10%–60% acetonitrile, 0.1% trifluoroacetic acid as described in Merrifield (1963) *J Am. Chem. Soc.* 85:2149–2154 and Lin et al. (1988) *Biochemistry* 27:5640–5645.

The peptides described herein were synthesized on a Gilson AMS-422 multiple peptide synthesizer using Fmoc amino acids. Gausepohl et al. (1992) *Peptide Res.* 5:315–320. Peptides were cleaved from the resin and deprotected by a 2-hr reaction with trifluoroacetic acid/water/thioanisole/ethanedithiol (100:5:5:2.5). the peptides were precipitated from ether, redissolved in formic acid, diluted with water, and lyophilized. Purification was achieved by reverse-phase high performance liquid chromatography using a gradient of acetonitrile in 0.1 % trifluoroacetic acid. All synthetic peptides were characterized by mass spectroscopy on a Bio-Ion 20 instrument and gave the expected molecular weight.

Murine 70Z/3 pre-B leukemia cells (ATCC T1D-158), H9 human lymphoma T-cells (ATCC CRL-8543), Jurkat human leukemia T-cells (ATCC T1B-152), and THP-1 human monocytic cells (ATCC T1B-202) were obtained from the American Type Culture Collection.

Expression of κ Ig, CD45, CD40, and the interleukin-2 receptor was assayed using standard enzyme-linked immunosorbent assays ("ELISAs") (see, Coligan et al. (eds.) (1991) *Current Protocols in Immunology*, Wiley & Sons, p. 2.10 or by FACS staining to measure cell-surface markers as described in Raff (1970) *Immunology* 19:637). Antibodies form cell surface markers were obtained from Pharmingen Co.

Amounts of TNF-α, IL-6, IL-8 and IL-10 were determined using the ELISA kits obtained from Genzyme following the manufacturer's instructions.

HIV-1 M1 p24 levels were assayed using the procedures described in Smithgall et al (1995) *AIDS Res. and Human*

*Retrovirus* 11:885. Proviral DNA content (gag) was measured using polymerase chain reaction analysis as described in Smithgall et al. (1995), supra.

2-LTR circles, a strictly nuclear form of HIV-1 DNA the expression of which indicates nuclear localization of the viral genome, was measured by as described in Bukrinsky et al (1991) *Science* 254:423.

EXAMPLE 1

Inhibition by the SV40MEM Polypeptide of κ Ig Light Chain Expression

This experiment was conducted to show that the polypeptide PKKKRKVAAVALLPAVLLALLAPKKKRKVC (SEQ ID NO:1) (the "SV40MEM" polypeptide), which comprises the hydrophobic region of the signal peptide from fibroblast growth factor and the SV40 large T antigen NLS, has immunosuppressive activity. The effect of the SV40MEM polypeptide was compared with two additional polypeptides, KKKYKAAVALLPAVLLALLAKKKYKC (SEQ ID NO:2) (the "HIV-1MEM" polypeptide), which is composed of the membrane translocation domain of FGF flanked by the NLS from the HIV-1 matrix protein and AKRVKLAAVALLPAVLLALLAKRVKLC (SEQ ID NO:3) (the "C-MYCMEM" polypeptide), which contains the NLS from the human c-myc oncoprotein (Chelsky et al. (1989), supra, and Dang et al. (1988), supra) using murine 70Z/3 pre-B cells.

Murine 70Z/3 cells (ATCC TlD-158) are a model cell line for analyzing the effects of compounds on B-cell differentiation. In response to *S. typhosa* LPS (Difco) or γ-interferon, these cells differentiate from surface κ immunoglobulin negative to κ Ig positive.

As seen in FIG. 1A, the SV40MEM polypeptide caused an approximately 75–80% inhibition of κ light chain expression in response to *S. typhosa* LPS (Difco) after a 1-hr pretreatment with the SV40MEM polypeptide. There was no effect of SV40MEM on the expression of CD45 or the interleukin-2 receptor. The maximum inhibitory effect occurred with an approximately 3-hr SV40MEM pretreatment. This inhibitory effect of the SV40MEM polypeptide can be overcome by increasing the concentration of LPS.

Figure 1B:
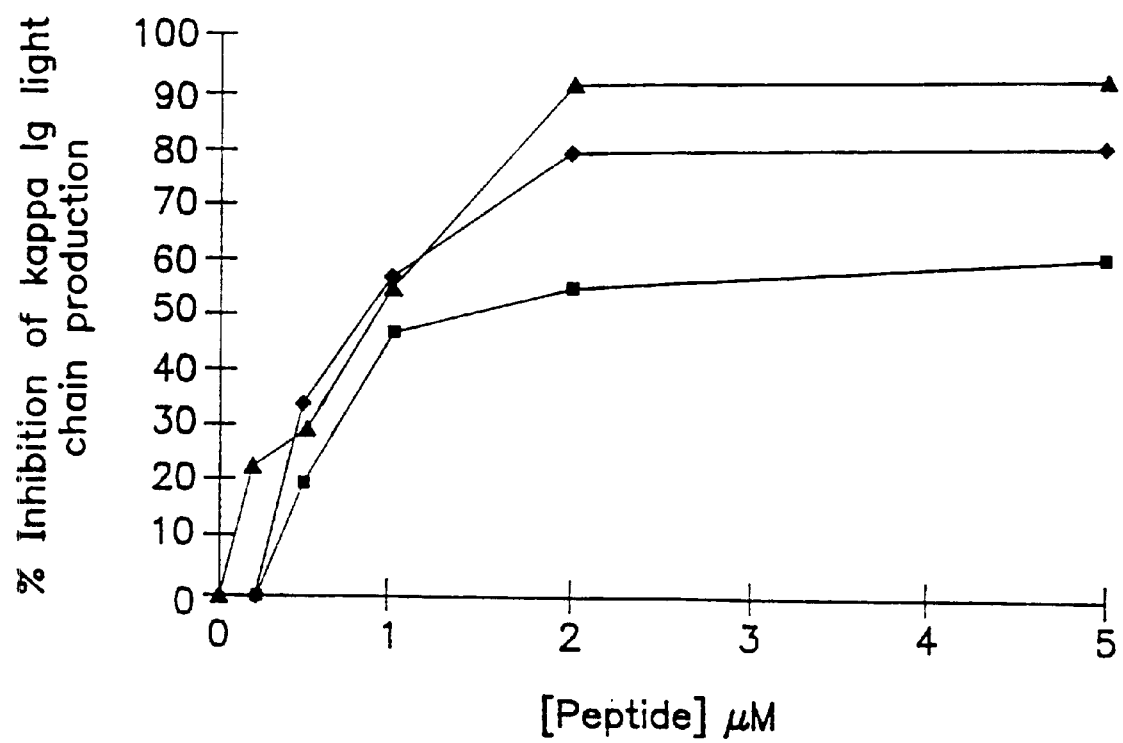
FIG. 1B is a graphical representation of the effect of three inhibitory polypeptides on LPS-stimulated κ Ig light chain production in 70Z/3 murine leukemia pre-B cells (diamonds: the SV40MEM polypeptide; squares: KKKYKAAVALLPAVLLALLAKKKYKC (SEQ ID NO:2) (the "HIV-1 MEM" polypeptide); triangles: AKRVKLAAVALLPAVLLALLAKRVKLC (SEQ ID NO:3) (the "C-MYCMEM" polypeptide)).

FIG. 1B depicts dose-response data for the effect of the D-amino acid form of the SV40MEM polypeptide compared with L-amino acid forms of the HIV-1MEM polypeptide and AKRVKLAAVALLPAVLLALLAKRVKLC (SEQ ID NO:3). These data show that the three polypeptides are approximately equally efficacious but that the latter two polypeptides are not as potent at inhibiting κ Ig light chain production as is SV40MEM. FIG. 1C shows that increasing the concentration of LPS can overcome the inhibitory effect of SV40MEM.

EXAMPLE 2

Inhibition by the SV40MEM Polypeptide of Cytokine Production

Figure 2:
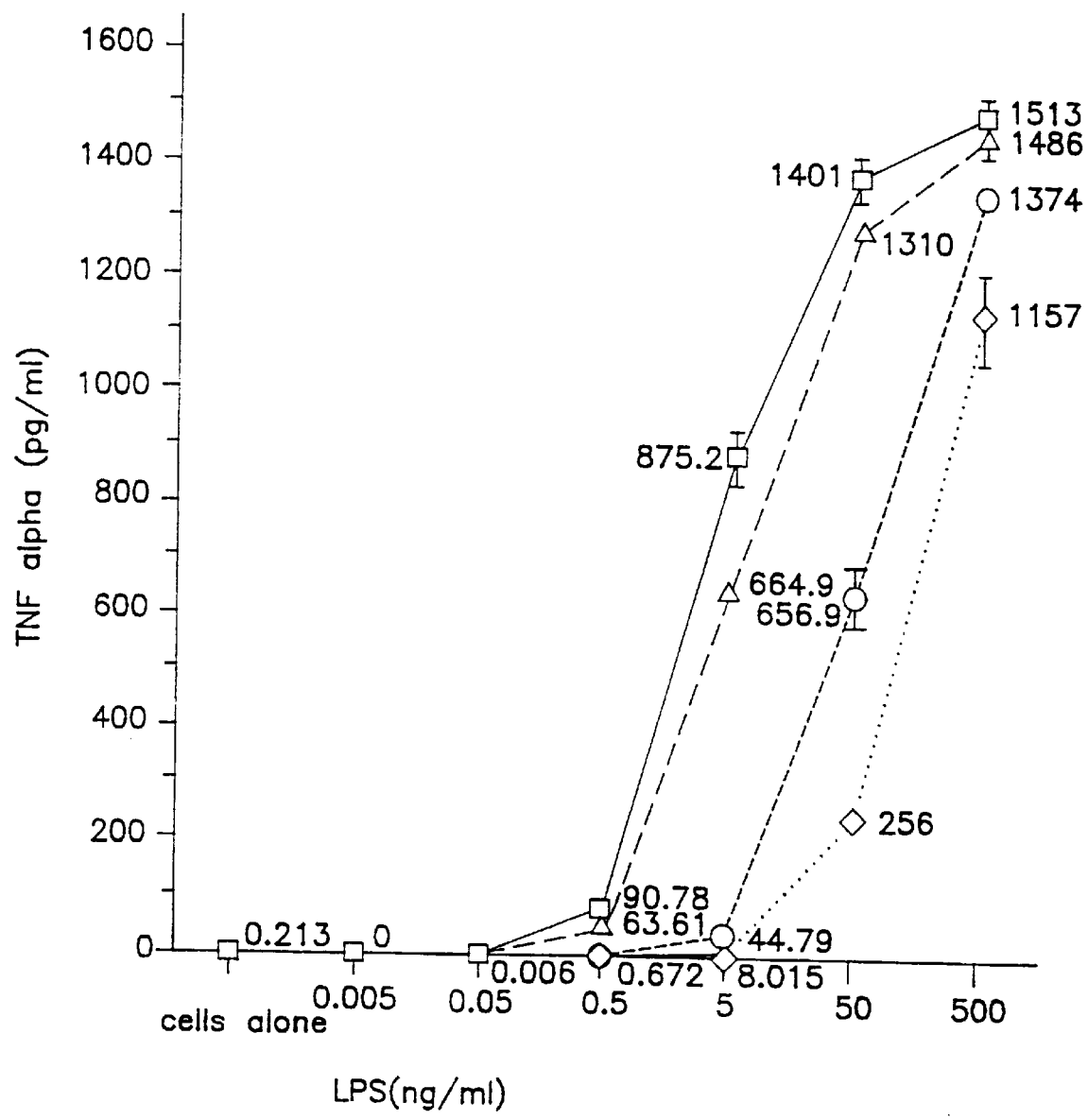
FIG. 2 is a graphical representation of the effect of the SV40MEM polypeptide on LPS-stimulated cytokine production in 70Z/3 murine leukemia pre-B cells (squares: untreated; diamonds: the SV40MEM polypeptide (10 μM); circles: the SV40MEM polypeptide (5 μM); triangles: the SV40 NLS (10 μM)).

THP-1 control cells were harvested, washed and set up in RPMI 1640, 10% fetal calf serum, at a concentration of 2.56×10$^6$ cells/ml. Phosphate buffered saline ("PBS") or one of the two respective polypeptides SV40MEM or SV40 (a peptide having only the SV40 large T antigen NLS sequence) were added to the cells at a concentration of 10 μM or 20 μM. The cells were then plated into a 96-well plate with 0.1 ml/well. The plate was then incubated for 2 hr at 37° C. in a 5% $CO_2$ atmosphere. Following the initial incubation, media or a titration of LPS was added to each of the wells in a volume of 0.1 ml. Thus, the final concentrations of polypeptides were 5 μM or 10 μM. Following 5 hr of LPS stimulation, supernatants were taken and TNF-α and IL-8 levels were determined by ELISA. In addition, cells treated with PBS or polypeptides, but not incubated with LPS, were removed at the time of supernatant removal to determine the viability of the cells following 7 hr of contact with the polypeptides. From the data depicted in FIG. 2, it can be seen that the SV40 polypeptide had no effect on TNF-α production but that the SV40MEM polypeptide inhibited TNF-α production in a dose-dependent manner. Similar results were obtained with respect to IL-8 production (data not shown).

EXAMPLE 3

Comparison of the Inhibition by the SV40MEM Polypeptide and other Inhibitory Polypeptides of κ Ig Light Chain Expression This experiment was conducted to compare the inhibitory effect of the SV40MEM polypeptide with that of the polypeptide AAVALLPAVLLALLAPVQRKRQKLMP (SEQ ID NO:5) (the "NF-κBMEM" polypeptide) on κ light chain expression in 70Z/3 B-cells.

The 70Z/3 cells were pretreated for 2 hr with between 0 and 50 μM of: (1) a peptide containing only the FGF signal sequence AAVALLPAVLLALLAP (SEQ ID NO:4) (the "MEM" peptide); (2) a polypeptide having the FGF signal sequence and the NLS of NF-κB p50 on the carboxy terminus of the signal sequence, namely, the NF-κBMEM polypeptide; (3) the SV40MEM polypeptide comprised of L-amino acids; or (4) the SV40MEM polypeptide comprised of D-amino acids. The cells were then incubated with LPS as described in Example 2 and assayed for expression of κ light chain expression.

Figure 3:
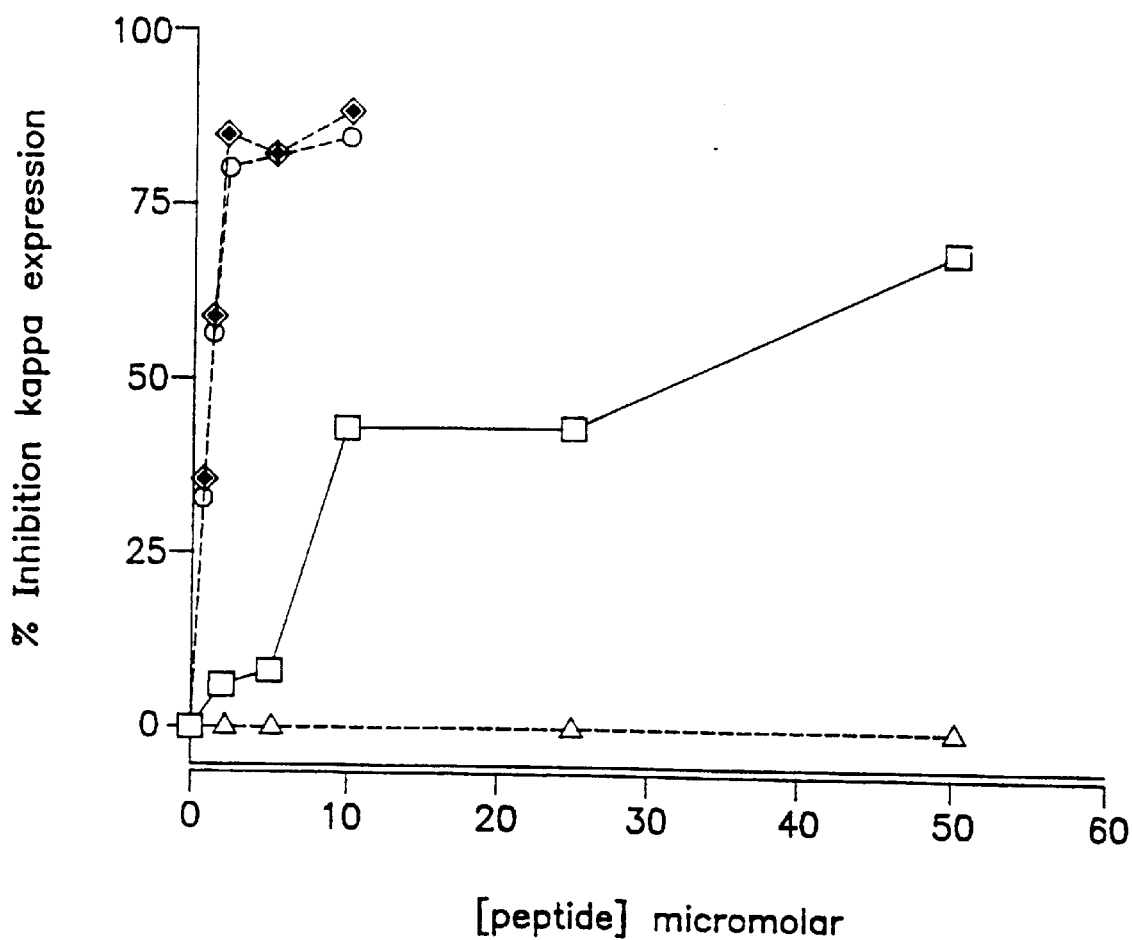
FIG. 3 is a graphical representation of dose-response relationships of three inhibitory polypeptides on LPS-stimulated κ Ig light chain production in 70Z/3 murine leukemia pre-B cells (triangles: a peptide containing only the fibroblast growth factor ("FGF") signal sequence AAVALLPAVLLALLAP (SEQ ID NO:4) (the "MEM" peptide); squares: a polypeptide having the FGF signal sequence and the NLS of NF-κB p50 on the carboxy terminus of the signal sequence, namely, AAVALLPAVLLALLAPVQRKRQKLMP (SEQ ID NO:5) polypeptide (the "NF-κBMEM" polypeptide); diamonds: the SV40MEM polypeptide comprised of L-amino acids; circles: the SV40MEM polypeptide comprised of D-amino acids.).

The data in FIG. 3 show that the L- and D-amino acid forms of the SV40MEM polypeptide were equally potent and efficacious with respect to inhibiting LPS-stimulated κ Ig expression. In addition, the data show that both the L- and D-amino acid forms of the SV40MEM polypeptide were more potent and more efficacious that the NF-κBMEM polypeptide having a single NLS sequence. The $EC_{50}$ for both the L- and D-amino acid forms of the SV40MEM polypeptide was 0.7 μM, while that for the NF-κBMEM polypeptide having a single NLS sequence was 32 μM.

EXAMPLE 4

Figure 4A:
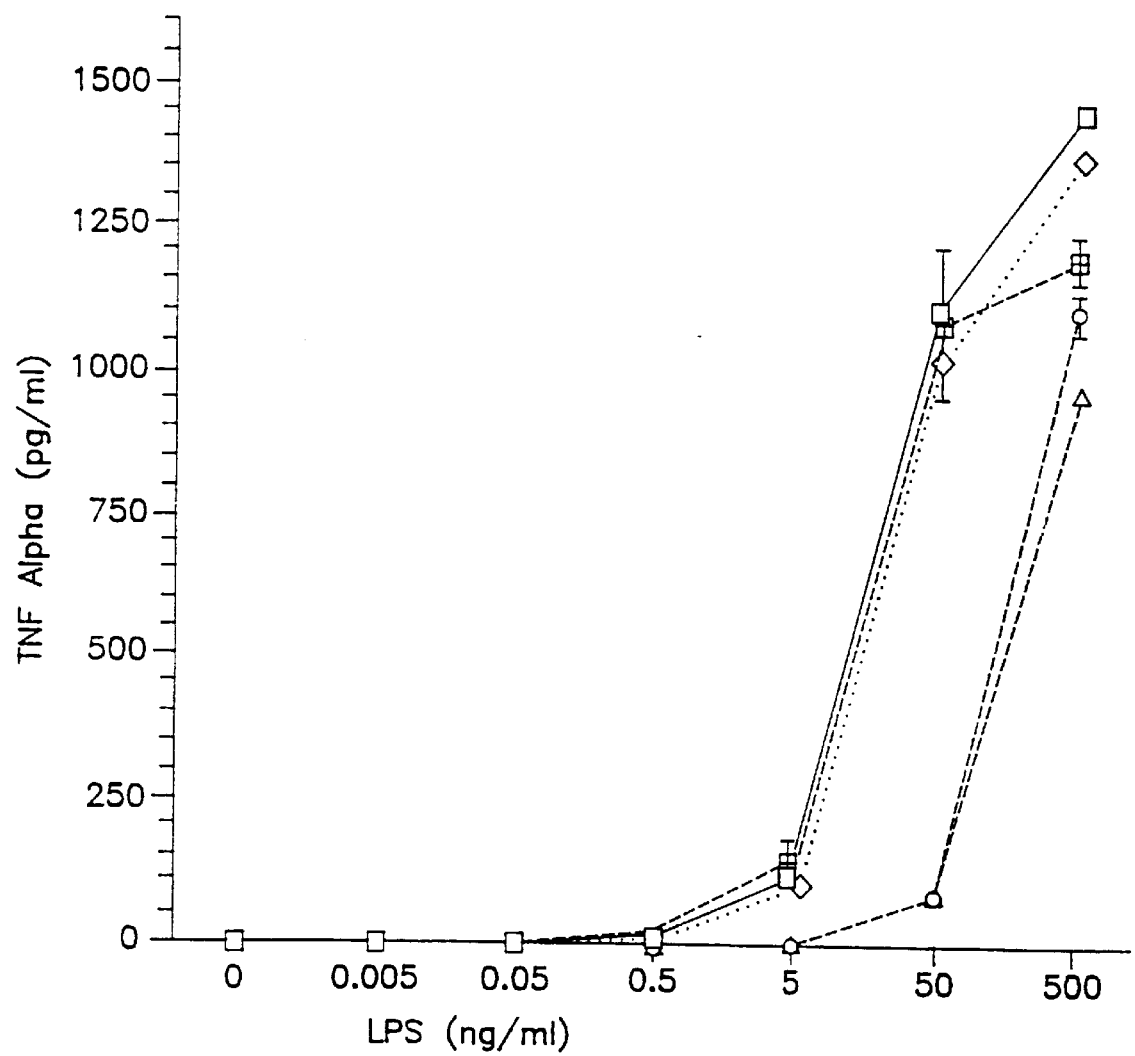
FIG. 4A is a graphical representation of the effect of inhibitory polypeptides on LPS-stimulated TNF-α production.
Figure 4B:
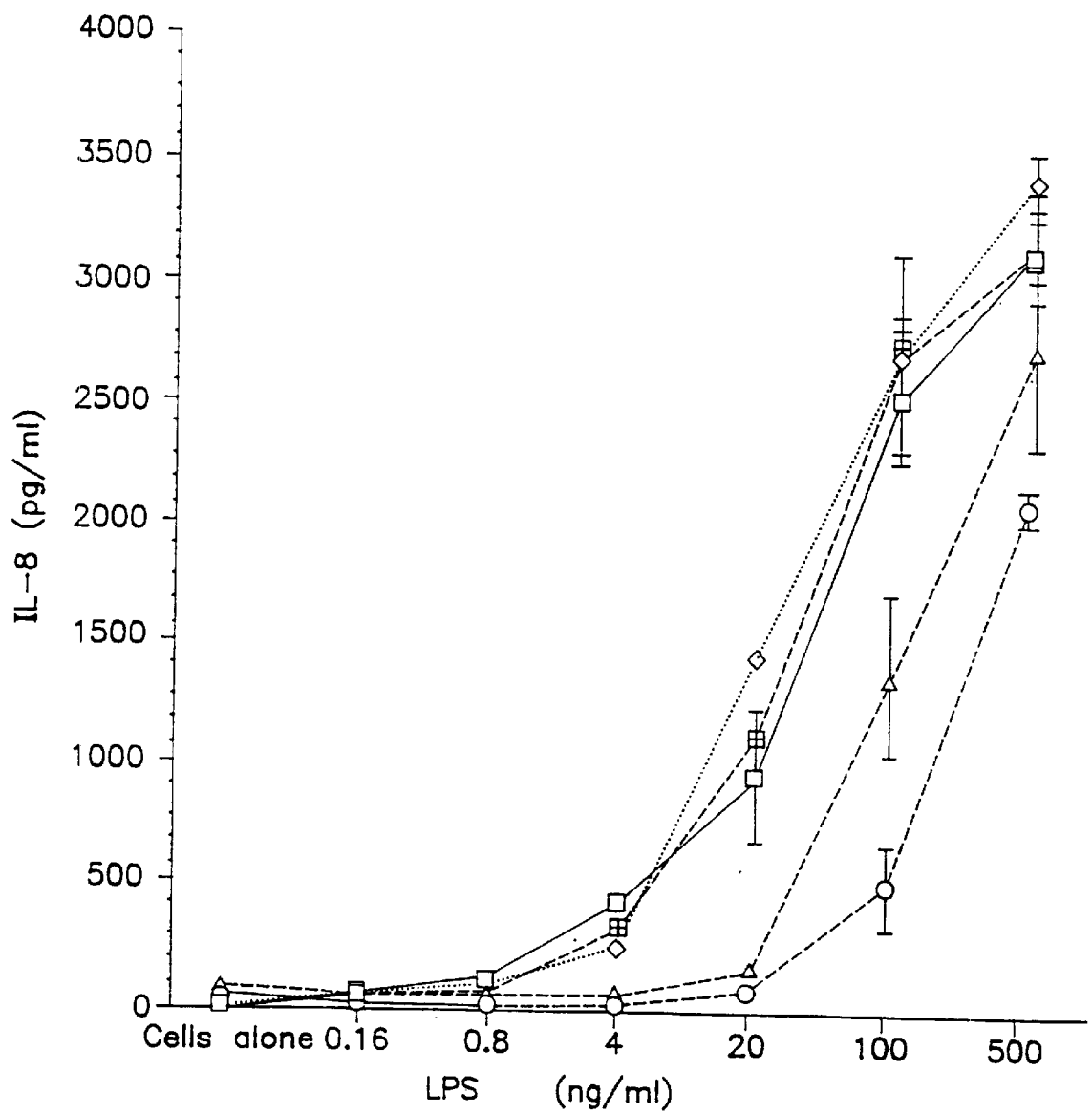
FIG. 4B is a graphical representation of the effect of inhibitory polypeptides on LPS-stimulated interleukin-8 ("IL-8") production. In both FIG. 4A and FIG. 4B the following symbols are used: squares—media control; crossed squares—the MEM peptide (5 μM); diamonds—the NF-κBMEM polypeptide (5 μM); circles—the SV40MEM polypeptide comprised of L-amino acids (5 1μM); and triangles—the SV40MEM polypeptide comprised of D-amino acids (5 μM).

Comparison of the Inhibition by the SV40MEM Polypeptide Other Inhibitory Polypeptides of Cytokine Production This experiment was conducted to compare the inhibitory effect of the SV40MEM polypeptide and other inhibitory polypeptides on LPS induction of cytokine production. THP-1 control cells (ATCC 9/95 stock) were harvested, washed and set up in RPMI 1640, 10% fetal calf serum as described in Example 2. The cells were incubated for 2 hr with PBS or (1) the FGF signal sequence, (2) a polypeptide having the FGF signal sequence and the NLS of NF-κB p50 on the carboxy terminus of the signal sequence, (3) the SV40MEM polypeptide comprised of L-amino acids, or (4) the SV40MEM polypeptide comprised of D-amino acids at a final concentration of 5 μM. The cells were then plated into a 96-well plate with 0.1 ml/well. The plate was then incubated for 2 hr at 37° C. in a 5% $CO_2$ atmosphere. Following the initial incubation, media or a titration of LPS was added to each of the wells in a volume of 0.01 ml/well. Following 5 hr of LPS stimulation, supernatants were taken and TNF-α levels were determined by ELISA. The data depicted in FIG. 4A indicated that only the L- or D-amino acid forms of the SV40MEM polypeptide significantly inhibited LPS-induced TNF-α expression; i.e., the polypeptide comprising the FGF signal sequence peptide and the NF-κB NLS did not significantly inhibit TNF-α expression. At high LPS concentrations, TNF-α was induced even in cells that had been incubated with the L- or D-amino acid forms of the SV40MEM polypeptide. Similar results were obtained with LPS-induced IL-8 production (FIG. 4B).

EXAMPLE 5

Effect of the SV40MEM Polypeptide on CD40 Expression

Figure 5A:
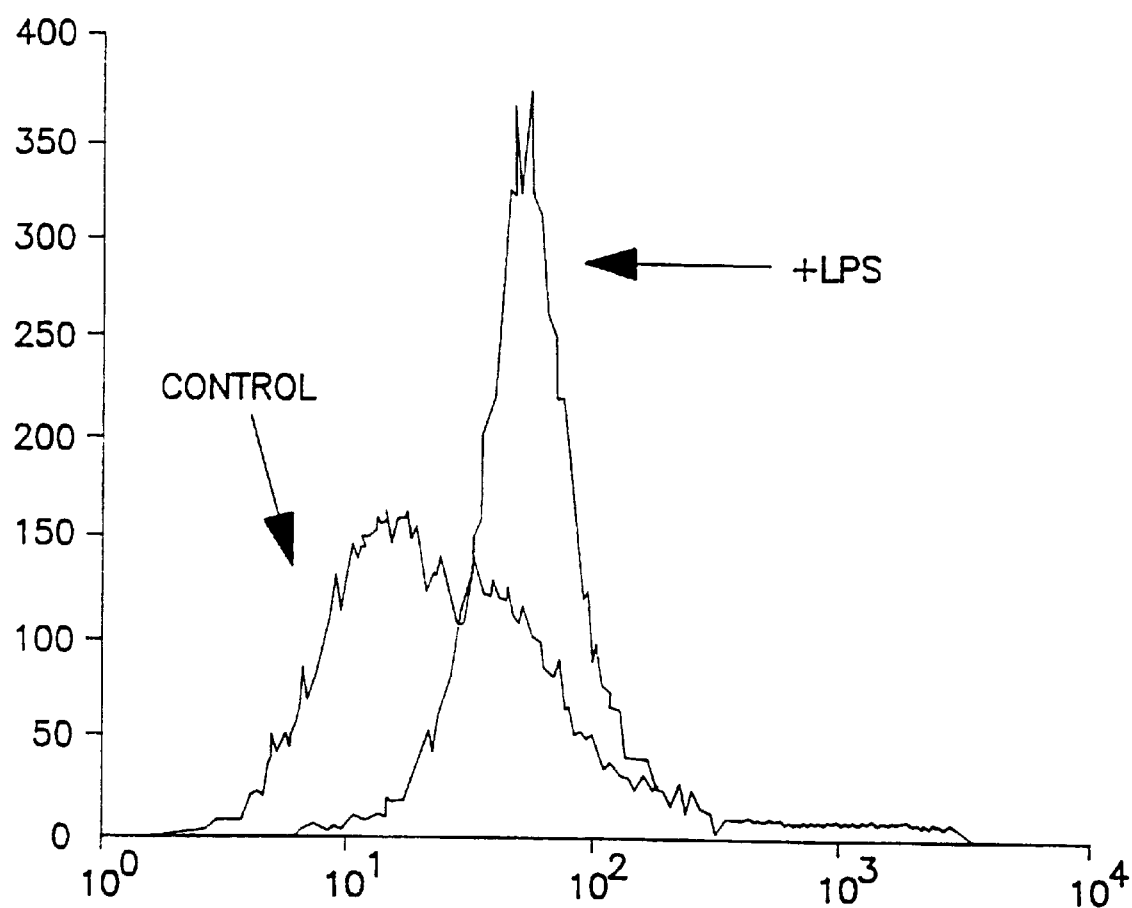
FIG. 5 is a graphical representation of the effect of the SV40MEM polypeptide on LPS-induced CD40 expression in 70Z/3 murine leukemia pre-B cells.
Figure 5B:
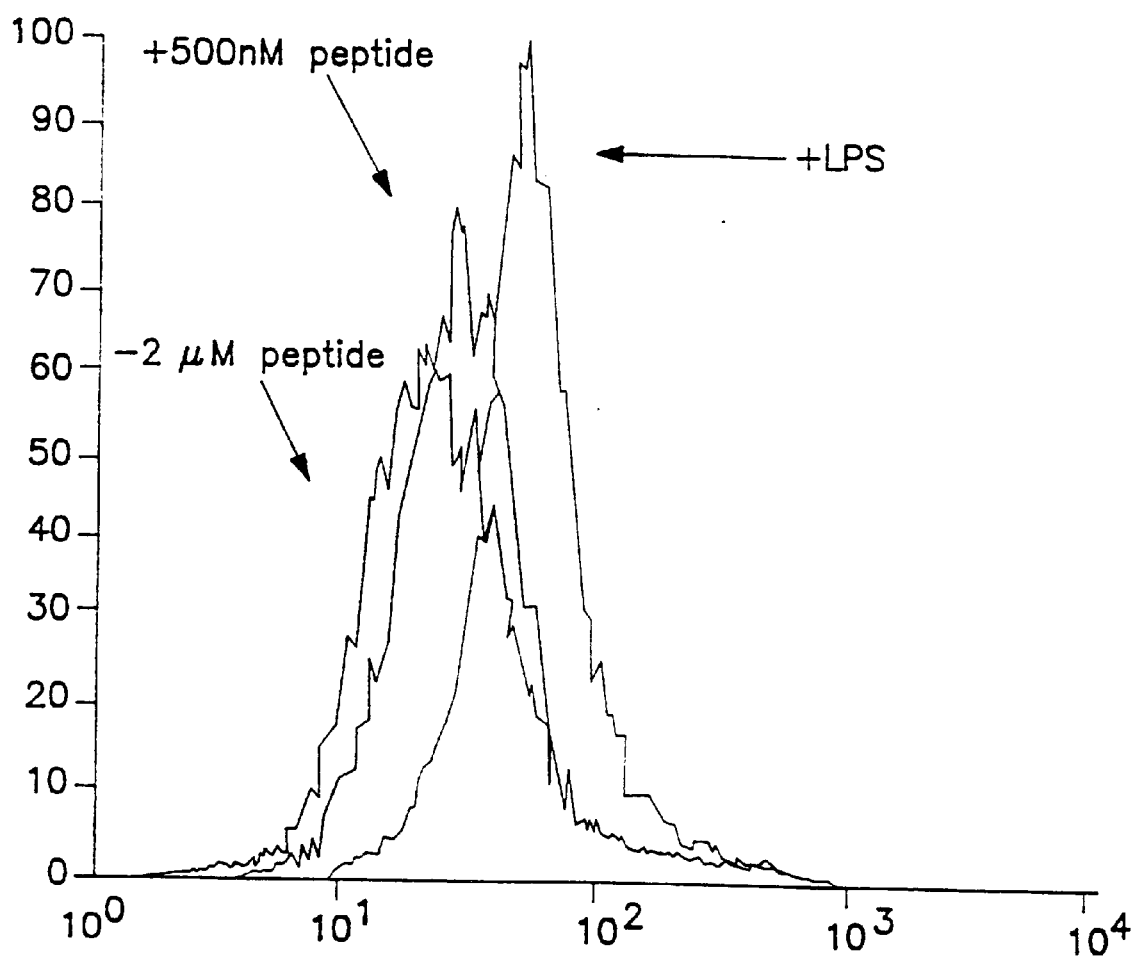

70Z/3 murine B-cells were treated with the SV40MEM polypeptide for 3 hr prior to activation with LPS. After activation with LPS, there was an approximately four-fold increase in CD40 expression above basal levels. The SV40MEM polypeptide inhibited this up-regulation of CD40 (see FIG. 5). These results indicate that the SV40MEM polypeptide should be efficacious at inhibiting B-cell responses in vivo.

EXAMPLE 6

Figure 6A:
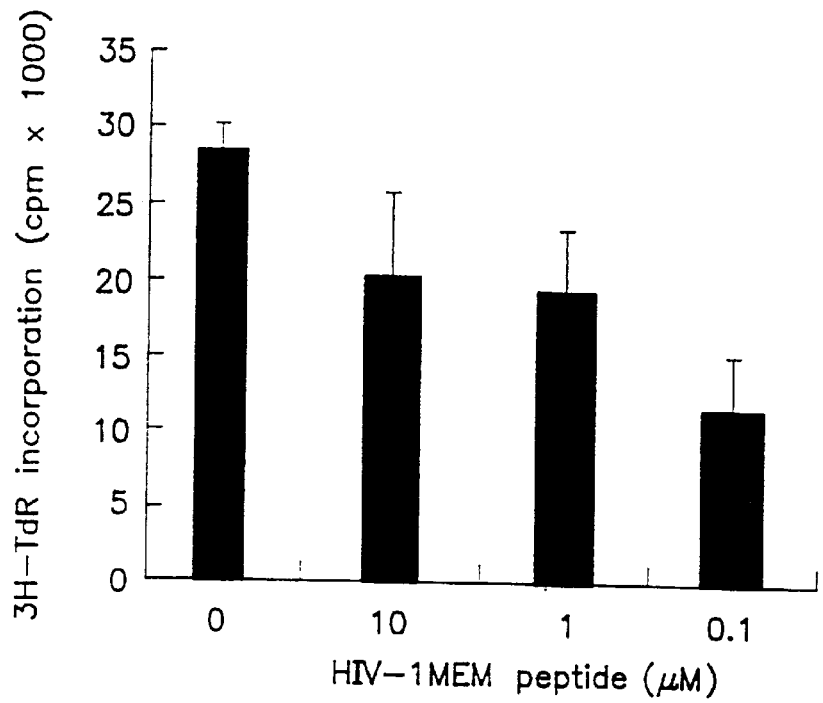
FIG. 6A is a graphical representation of the effect of the HIV-1MEM polypeptide on $^3$H-deoxyribothymidine uptake into peripheral blood mononuclear cells ("PBMCs").
Figure 6B:
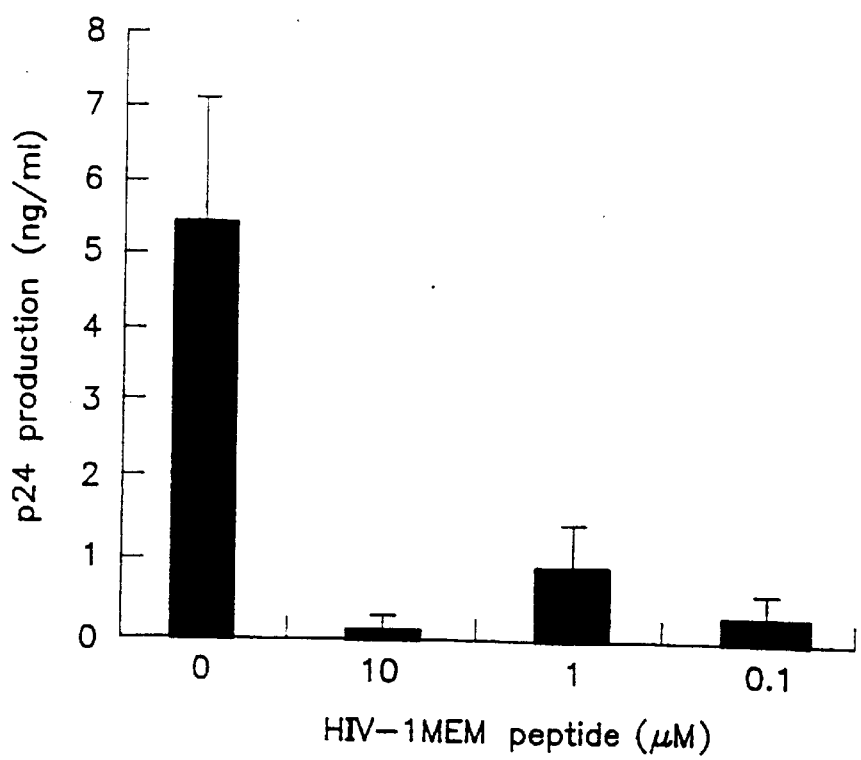
FIG. 6B is a graphical representation of the effect of HIV-1MEM on viral p24 production in anti-CD3 stimulated PBMCs infected with HIV-1 primary isolate M1.
Figure 6C:
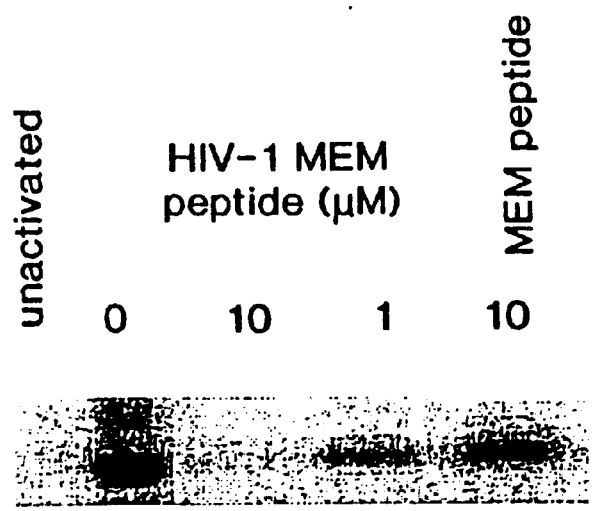
FIG. 6C is a photograph of a gel depicting the effect of HIV-1MEM polypeptide on the expression of proviral gag sequences in anti-CD3 activated PBMCs infected with HIV-1 primary isolate M1.

Inhibition of Infection of Peripheral Blood Mononuclear Cells with the Primary Isolate of HIV-1 M1 by the HIV-1 MEM Polypeptide PBMCs were obtained washed, cultured, and infected with HIV-1 as described in Dubrovsky et al. (1995) *Mol. Med.* 1:217–230). PBMCs from a seronegative donor were collected and depleted of CD8$^+$T cells by negative selection. The cells were activated with an anti-CD3 monoclonal antibody prepared according to the method described in Wee et al. (1993) *J. Exp. Med.* 177:219 and incubated for 3 hr with the HIV-1MEM polypeptide. The cells were then incubated with M1 virus isolated from PBMC collected from HIV-infected donors in the presence of inhibitors for 2 hr. The virus was washed out, and the cultures supplemented with the appropriate inhibitor and allowed to incubate for seven days. Virus production was determined by measuring the p24 levels in the culture supernatant (FIG. 6B) and contrasted with the effect of the polypeptide on cell proliferation (FIG. 6A), which virus load was determined by polymerase chain reaction analysis of proviral DNA content (gag) (FIG. 6C). The MEM peptide represents the FGF membrane translocating portion of the HIV-1MEM polypeptide. The HIV-1MEM polypeptide significantly reduced the virus load and virus production compared to untreated but activated cultures.

EXAMPLE 7

Figure 7:
FIG. 7 is a photograph of a gel depicting the results of a polymerase chain reaction analysis of the effect of HIV-1MEM polypeptide on the expression of proviral gag sequences in H9 human lymphoma T-cells or Jurkat human leukemia T-cells infected with HIV-1 primary isolate M1.

Inhibition of Infection of T Cells with HIV$_{M1}$ Virus by the HIV-1MEM Polypeptide H9 and Jurkat cells were incubated with the HIV-1MEM polypeptide (2 μM) or the control MEM peptide for 4 hr prior to addition of HIV-M1 virus. Cells were harvested on day 3 following injection and the level of HIV-1 DNA evaluated by polymerase chain reaction. As shown in FIG. 7, the HIV-1MEM polypeptide inhibited infection of both cells lines as determined by the lower levels of HIV-1 DNA compared to untreated and MEM peptide-treated cultures.

EXAMPLE 8

Figure 8A:
FIG. 8A is a photograph of gels depicting the results of polymerase chain analyses of the effect of HIV-1MEM and the NF-κBMEM polypeptide on the expression of proviral gag sequences in Jurkat T-cells infected with $HIV_{LAI}$.
Figure 8B:
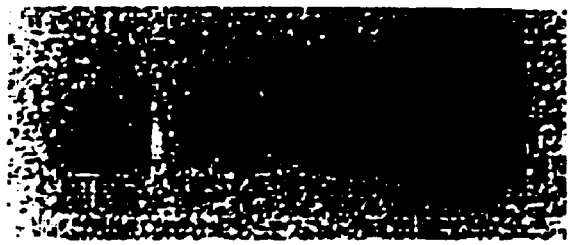
FIG. 8B is a photograph of gels depicting the results of polymerase chain analyses of the effect of HIV-1MEM and the NF-κBMEM polypeptide on the expression of 2-long terminal repeat ("LTR") circles in Jurkat T-cells infected with $HIV_{LAI}$.

Reduction in Viral Infection Due to Reduction in Nuclear Translocation of HIV Genome Jurkat cells were incubated with the SV40MEM polypeptide for 3 hr with HIV$_{LAI}$ for 1–2 hr. The virus was washed out and the cultures supplemented with the appropriate inhibitor (SV40MEM, 0.1 μM and 1.0 μM; NF-κBMEM, 10 μM). After 24 hr, the cells were collected, lysed and evaluated for HIV-1 DNA by polymerase chain reaction analysis of gag sequences (see FIG. 8A) and 2-LTR circles (see FIG. 8B). The uniform signal achieved in all samples when assayed for gag sequences shows that all cultures internalized virus relatively equally and allowed formation of the viral cDNA in the cytoplasm. The difference in the levels of 2-LTR circles shows that SV40MEM inhibited translocation of the viral genome into the nucleus. Thus, the polypeptides do not affect virus entry into cells but, as predicted, specifically target nuclear translocation. The NF-κBMEM peptide showed no effect on viral internalization or translocation of the viral genome into the nucleus.

EXAMPLE 9

Effect of SV40MEM on Proliferation of 70Z/3 Murine B-cell Leukemia Cells

Figure 9:
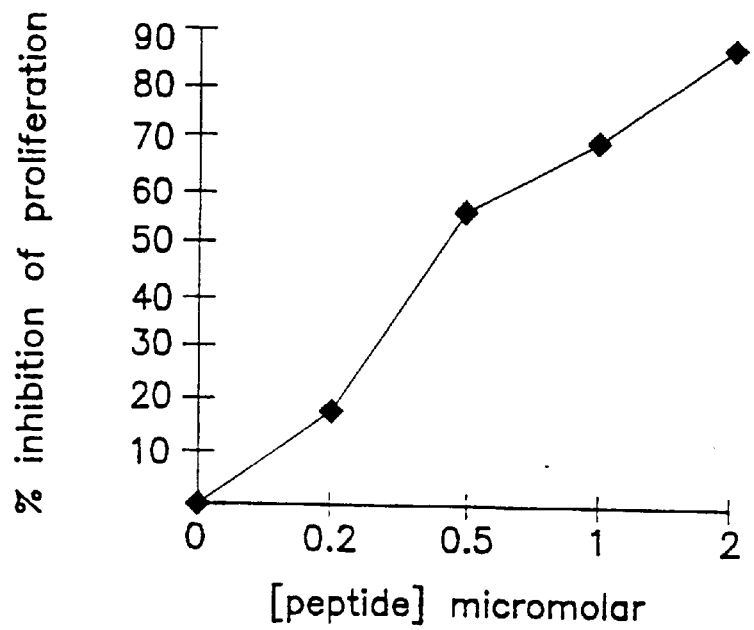
FIG. 9 is a graphical representation of the effect of SV40MEM prepared from D-amino acids on proliferation of 70Z/3 murine leukemia pre-B cells.

Murine 70Z/3 B-cells were treated with 0, 0.2, 0.5, 1, or 2 μM SV42MEM prepared from D-amino acids. On day 0, the cell concentrations of the control and treated cells were the same. After 48 hr of exposure to the peptide, the treated cells were again counted and compared to control cells. FIG. 9 shows that the proliferation of the murine leukemia cell line was inhibited by the lowest concentration (0.2 μM) of D-SV40MEM tested and was 90% inhibited by the highest concentration tested (2 μM).

EXAMPLE 10

Effect of SV40MEM on Proliferation of RAJI Human B-cell Leukemia Cells

Figure 10:
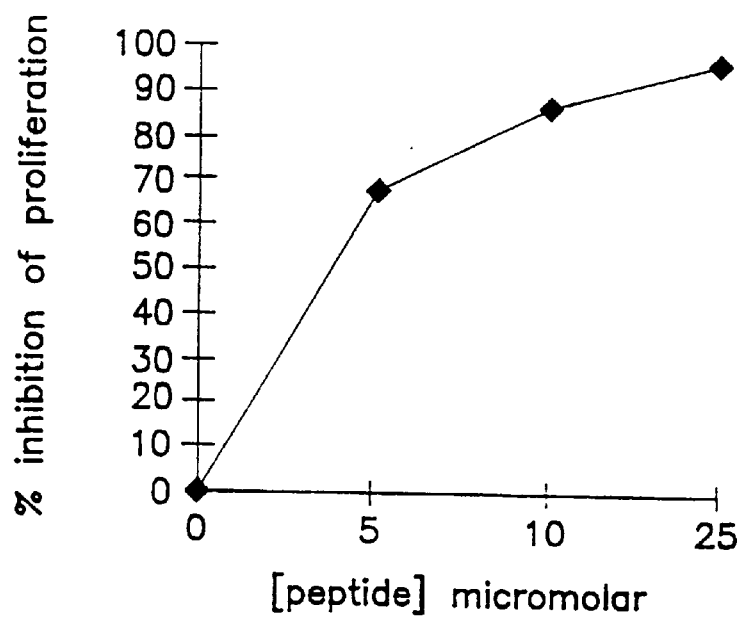
FIG. 10 is a graphical representation of the effect of SV40MEM prepared from D-amino acids on proliferation of RAJI human B-cell leukemia cell line.

Human RAJI B-cells were treated with 0, 5, 10 or 25 μM SV40MEM prepared from D-amino acids. On day 0, the cell concentrations of the control and treated cells were the same. After 48 hr of exposure to the peptide, the treated cells were again counted and compared to control cells. FIG. 10 shows that the proliferation of the murine leukemia cell line was inhibited by the lowest concentration (5 μM) of D-SV40MEM tested and was greater than 95% inhibited by the highest concentration tested (25 μM).

EXAMPLE 11

In Vivo Immunosuppressive Effect of the SV40MEM Polypeptide In a Murine Sheep Red Blood Cell Assay Female BALB/c mice (6–8 weeks of age) were housed in groups of 5 in Thorne units with ad libitum access to food and water. Mice were immunized on day 0 by intravenous (IV) injection of 1×10$^8$ sheep red blood cells ("SRBCs"). The mice were then divided into groups of five and control solutions or inhibitory peptides were administered at various doses, either by IV injection or orally ("PO") by gavage with a 24-gauge feeding tube and routes.

The SV40MEM polypeptide was administered either intravenously (IV) or orally (PO) with the following schedule: IV administration of 5 mg/kg on days 0, 1, 2, and 3; PO administration of 1 mg/kg on days 0, 1, 2, 3, and 4. After 14 days, the mice were bled from the orbital sinus and the level of anti-SRBC antibodies were measured in the serum by ELISA. Briefly, Immulon 2 plates (Dynatech) were coated with SRBC membrane antigen (*Anal. Biochem.* 82:362–371 (1978)) at 5 μg/ml in 0.05 M carbonate/bicarbonate buffer (pH 9.6) and incubated overnight at 2–8° C. Plates were blocked for 1-hr at room temperature with Specimen Diluent Concentrate (Genetic Systems, Redmond, Wash.) diluted 1:10 with distilled water. The plates were washed in phosphate-buffered saline and 0.05% Tween-20 ("PBS/Tween"). Serum samples were diluted in Specimen Diluent and incubated for 1 hr at room temperature. After washing the plates in PBS/Tween, goat anti-mouse IgG1-horse radish peroxidase-conjugated ("IgG1-HRP") antibody (Southern Biotechnology, Birmingham Ala.) was added at 1:5000 dilution and incubated for 1 hr at room temperature. Plates were washed and conjugate binding was detected using 3,3',5,5'-tetramethylbenzidine ("TMB") (Genetic Systems) as the substrate. TMB was added and incubated for 15 min at room temperature. The reaction was stopped by the addition of 3 N $H_2SO_4$. Absorbance at 45 nm was recorded from duplicate samples using a microtiter plate reader (Bio Tek Instruments).

Figure 11A:
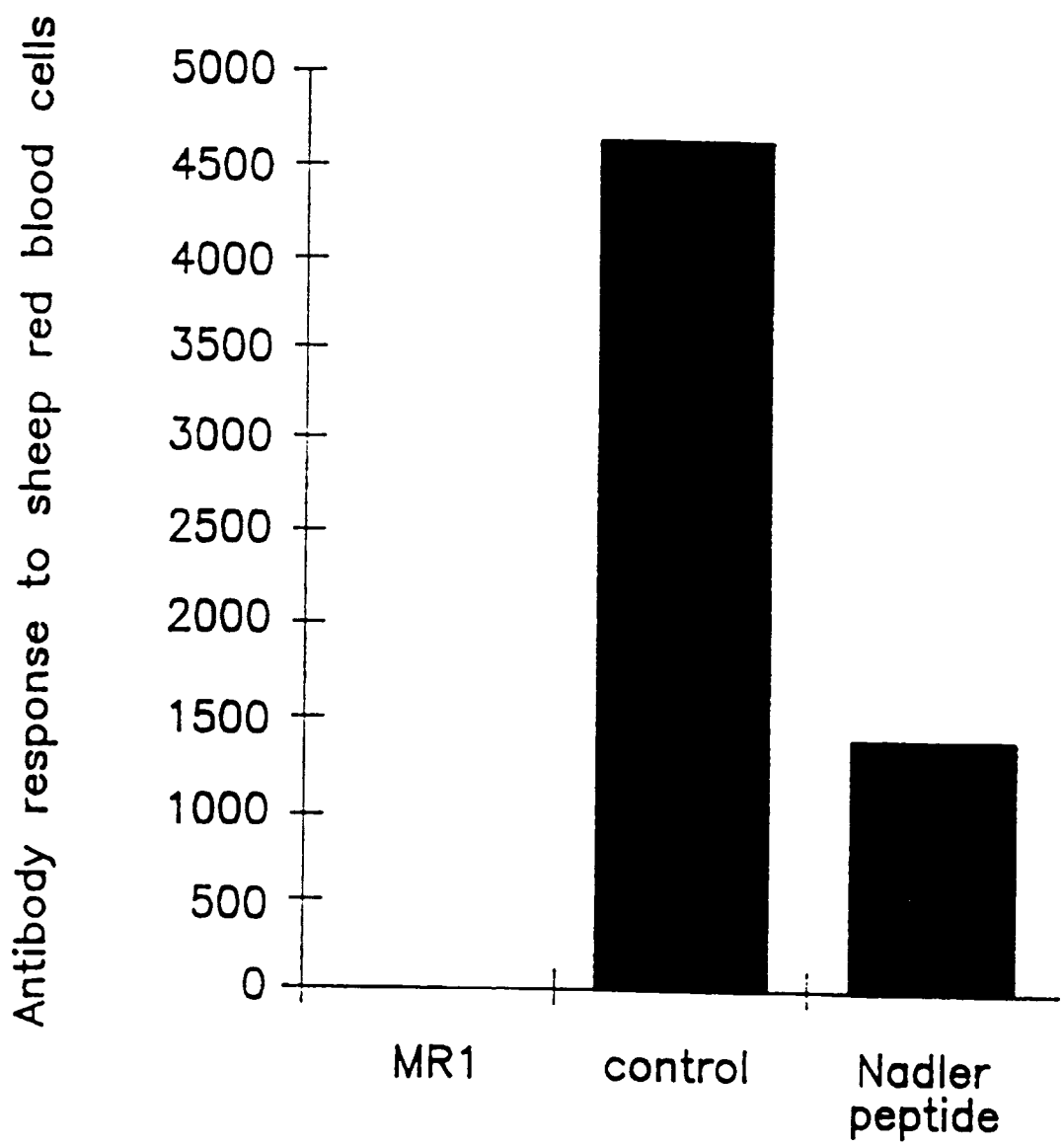
FIG. 11A is a graphical representation of the effect of an intravenous administration of the SV40MEM polypeptide on the in vivo response of mice to sheep red blood cells.
Figure 11B:
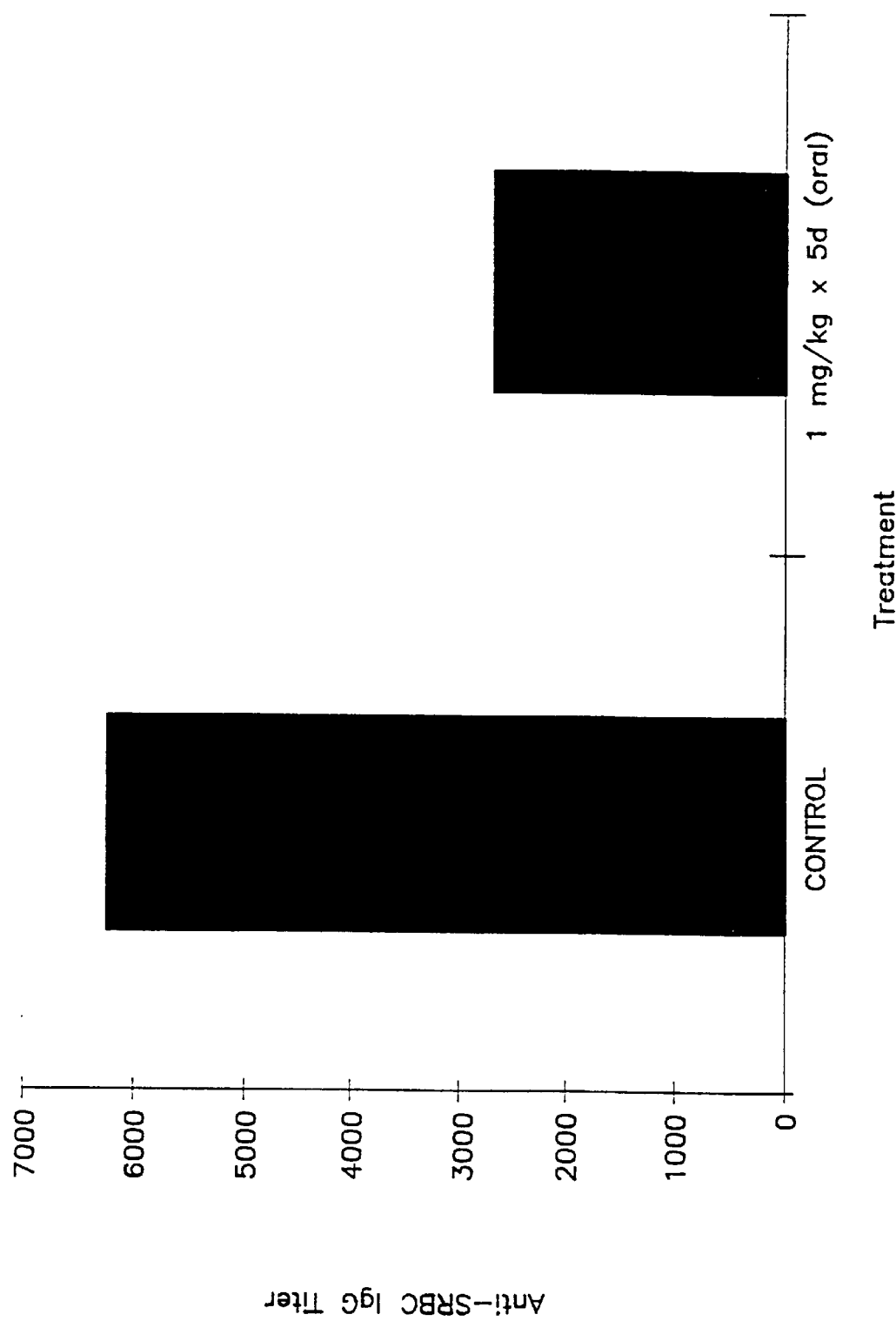
FIG. 11B is a graphical representation of the effect of an oral administration of the SV40MEM polypeptide on the in vivo response of mice to sheep red blood cells.

The results presented in FIG. 11A and FIG. 11B show that, while there was no effect on total IgG levels in the mice receiving the SV40MEM polypeptide either IV or PO, the polypeptide inhibited the specific anti-SRBC response when administered either IV or PO.

EXAMPLE 12

Comparison of the Inhibition by the BMS-205820 Polypeptide and other Inhibitory Polypeptides of the Anti-Hemocyanin Response in Mice Female BALB/c mice (8 weeks of age) were immunized by intraperitoneal injection of 25 μg keyhole limpet (*Megathura crenulata*) hemocyanin ("KLH") (Pacific Bio-Marine Laboratories, Venice, Calif.) without adjuvant on day 0. Mice were divided into groups of five and inhibitory peptides C-MYCMEM and BMS-205820 (PKKKRKVAAVALLPAVLLALLAPKKKRKV (SEQ ID NO:24)), which is identical to the SV40MEM polypeptide with the exception that the polypeptide lacks the C-terminal cysteine, were administered on day 0 at 5 mg/kg, followed by 5 subsequent doses of the same concentration every other day. Control mice were treated with a single 200-μg dose of Chimeric L6 antibody ("Chi L6"). After 14 days, the mice were bled from the orbital sinus and the level of anti-KLH antibodies were measured in the serum by ELISA as described in Example 11.

Figure 12:
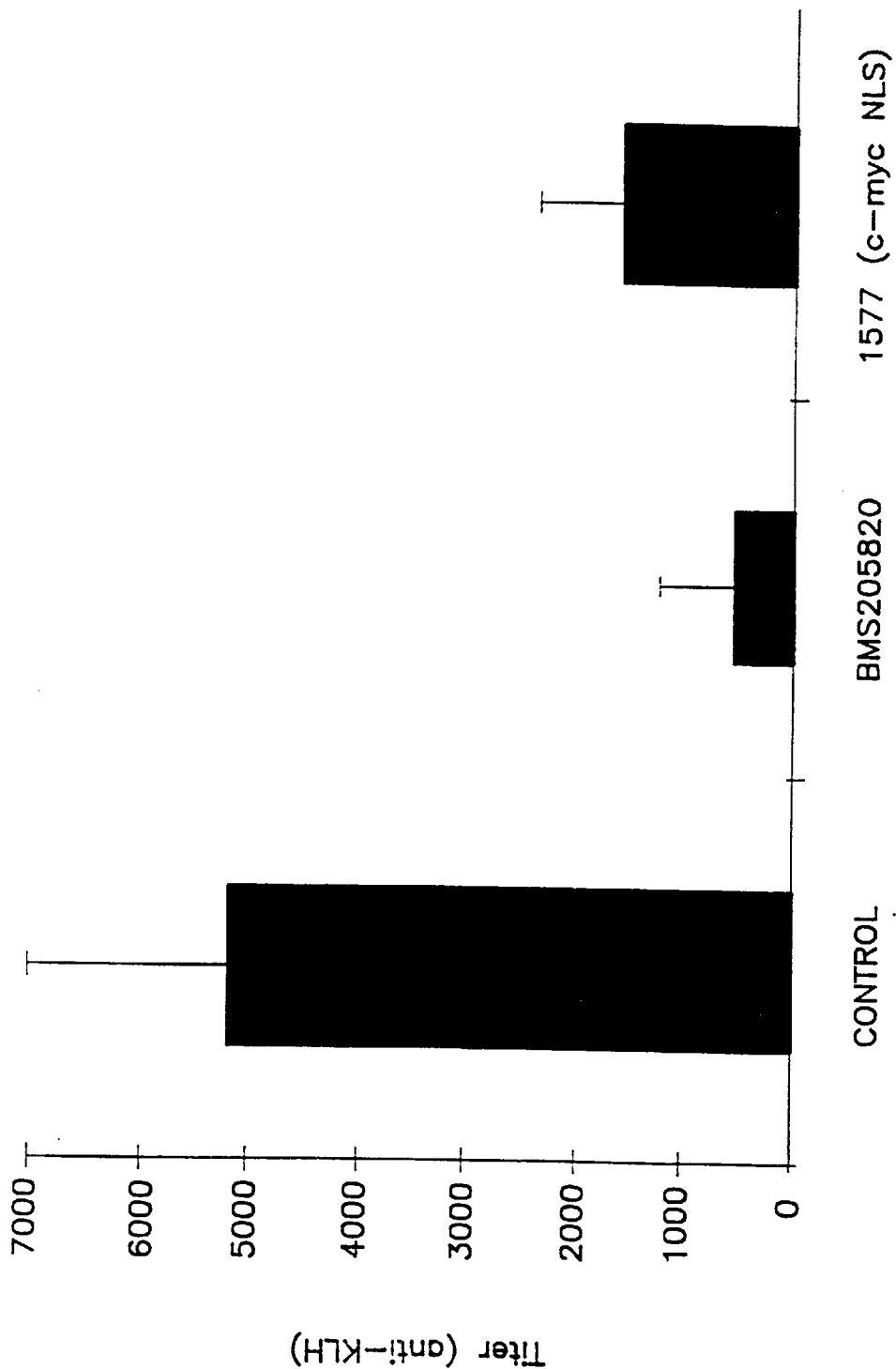
FIG. 12 shows the effect of BMS-205820 and C-MYCMEM (BMS-214572) on the anti-hemocyanin (KLH) response in mice.

Both the BMS-205820 and the C-MYCMEM polypeptide inhibited the specific anti-KLH response (see FIG. 12).

EXAMPLE 13

Stimulation of Apoptosis by the SV40MEM Polypeptide in Anti-CD3-treated Jurkat T-Cells A 24-hr incubation of Jurkat T-cells with SV40MEM and anti-CD3, caused greater than 85% of the cells to apoptose. Neither SV40MEM nor anti-CD3 alone caused significant apoptosis.

EXAMPLE 14

Inhibition of IKB Degradation by the SV40MEM Polypeptide

IκB is an inhibitor of NF-κB nuclear translocation. When cells are activated by the appropriate proinflammatory stimulus, e.g., cytokines or LPS, IκB is degraded. This results in the unmasking of the NLS of NF-κB. thereby allowing NF-κB to be translocated into the nucleus. This experiment was done to explore the effect of the SV40MEM polypeptide on IKB degradation in murine 70Z/3 cells.

Murine 70Z/3 cells ($5 \times 10^7$ cells) were incubated with the SV40MEM polypeptide (2 μM) or PBS. The two groups of cells were subdivided into aliquots and activated with LPS (100 ng/ml) for 0, 15, 30, 60, or 120 min. The cells were lysed in 200 μL lysing buffer (20 mM N-(2-hydroxyethyl) piperazine-N'-(2-ethanesulfonic acid) ("HEPES"), pH 7.2, 20 mM NaCl, 2.5 mM $MgCl_2$, 0.1% nonylphenoxy polyethoxy ethanol ("NP-40")). The lysates were frozen until analyzed for the presence of IκB by Western analysis using an antibody directed to the carboxy terminus of IκB (Santa Cruz Corp., Santa Cruz, Calif.) according to the manufacturer's instructions.

Degradation of IκB was apparent after 15-min activation of the control cells with LPS. There was no apparent degradation of IκB in cells pretreated with the SV40MEM peptide.

EXAMPLE 15

Ability of BMS-205820 to Treat Septic Shock

These experiments show that BMS-205820 is efficacious for the treatment of septic shock. A lethal model of septic shock was used as follows.

A. Balb/c mice were pretreated with either 5 mg/kg BMS-205820 or PBS, intravenously at 1 and 3 hours, prior to injection with 200 mg lipopolysaccharide (LPS), the causative agent of septic shock. LPS was administered intraperitoneally. Mice were given another injection of the polypeptide immediately after the LPS injection, as well as 24 hours after the LPS injection. Mice typically died within 48 hours of the LPS injection. As can be seen in Table 1, in two separate experiments, administration of BMS-205820 significantly increased the number of mice surviving seven days post-LPS injection.

TABLE 1

| | Fraction of Mice Surviving Seven Days Post LPS Injection | |
|---|---|---|
| Experiment | LPS + PBS | LPS + BMS-205820 |
| 1 | 0/10 | 6/10 |
| 2 | 2/10 | 10/10 |

B. Balb/c were treated with 200 μg of LPS followed by the BMS-205820 polypeptide, at the times indicated in Table 2. The BMS polypeptide was administered intravenously and the LPS was administered intraperitoneally. Group A mice were treated with 5 mg/kg of polypeptide in PBS at the indicated times, post-LPS administration. Group B mice received an additional dose of polypeptide 3 hours post-LPS treatment.

As can be seen in Table 2, BMS-205820 was effective in inhibiting death in response to LPS, especially when two doses of polypeptide were administered.

TABLE 2

Effect of Delayed Treatment with BMS 205820
in a Lethal Model of Septic Shock

|  | Fraction Surviving | |
| --- | --- | --- |
| Treatment | Group A | Group B |
| None | 0/5 | 2/5 |
| T = 0 | 5/5 | 5/5 |
| T = 30 min. | 1/5 | 5/5 |
| T = 1 hr. | 2/5 | 5/5 |
| T = 1.5 hr. | 1/5 | 4/5 |
| T = 2 hr. | 0/5 | 0/5 |

EXAMPLE 16

Inhibition of Cytokine Production in vivo by the BMS-205820 Polypeptide

These experiments show that the BMS-205820 polypeptide is capable of modulating cytokine production. In particular, a non-lethal model of septic shock was used. Balb/c mice were treated with 1 μg LPS, and at the same time, a single dose of 3 mg/kg of the BMS-205820 polypeptide in PBS. TNF-α, IL-6 and IL-10 levels were measured in serum by ELISA.

Figure 13A:
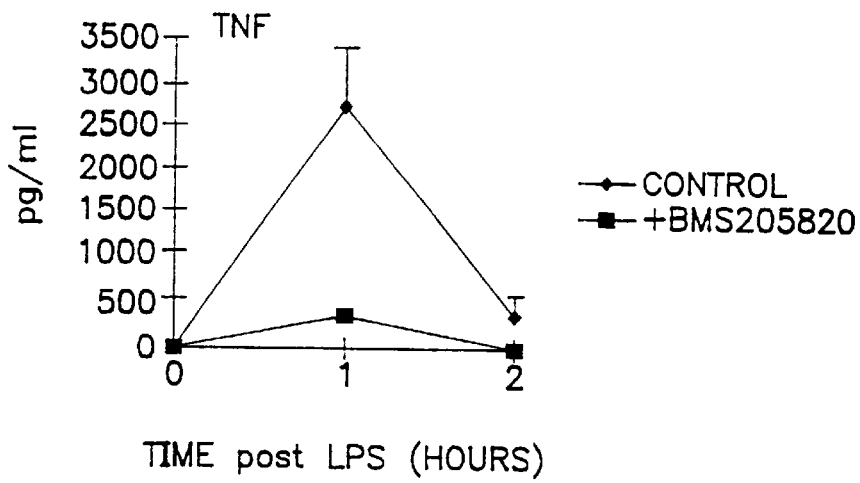
FIG. 13A, shows the effect of the BMS-205820 polypeptide on the production of TNF-α in vivo.
Figure 13B:
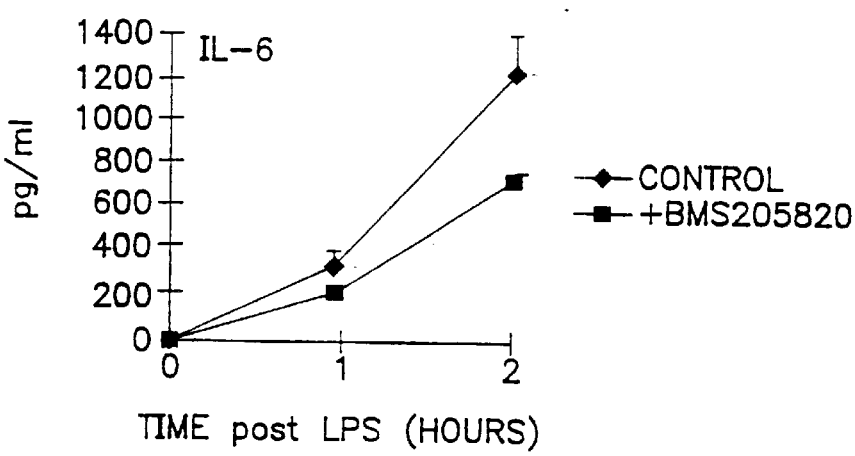
FIG. 13B shows the effect of the BMS-205820 polypeptide on the production of IL-6 in vivo.
Figure 13C:
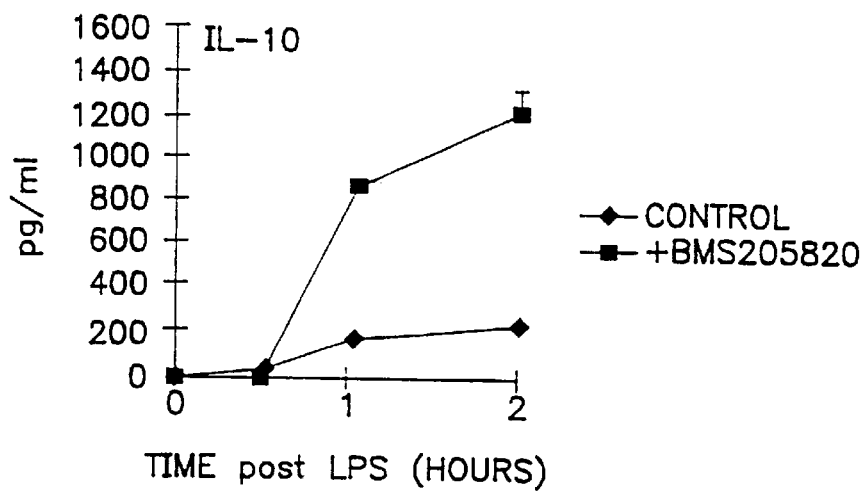
FIG. 13C shows the effect of the BMS-205820 polypeptide on the production of IL-10 in vivo.

As shown in FIG. 13A, the BMS-205820 polypeptide caused a significant inhibition in the production of TNF-α, which is a major contributor to the sepsis syndrome. IL-6 levels were only slightly affected (FIG. 13B), whereas IL-10 production was greatly increased (FIG. 13C). The effect on IL-10 is beneficial since this cytokine is immunosuppressive and has been shown to have efficacy in models of septic shock.

EXAMPLE 17

Inhibition of LPS Binding to CD14 Using BMS-205820 and C-MYCMEM

These experiments show that BMS-205820 and C-MYCMEM (the "BMS-214572" polypeptide) are both capable of inhibiting the binding of LPS to its cell surface receptor, CD14, evidencing that the polypeptide inhibitors are useful in the treatment of sepsis.

96-well plates were coated with goat-anti human Ig, soluble CD-1 4 Ig was added, and the plates were incubated overnight at 4° C. The BMS polypeptide, the C-MYCMEM polypeptide, an SV40 NLS polypeptide containing a single SV40 large T-antigen NLS, a c-myc NLS without a translocation sequence (AKRVKL (SEQ ID NO:6)), a control non-NLS polypeptide, 377G, or PBS, were added to the plates and the plates were incubated for 5 min. E. coli AO16 LPS was then added to the plates and the plates were incubated for 2 hours at 4° C. The plates were washed and LPS was detected using 0.5 μg/ml mouse anti-E. coli LPS, followed by goat anti-mouse horseradish peroxidase.

Figure 14:
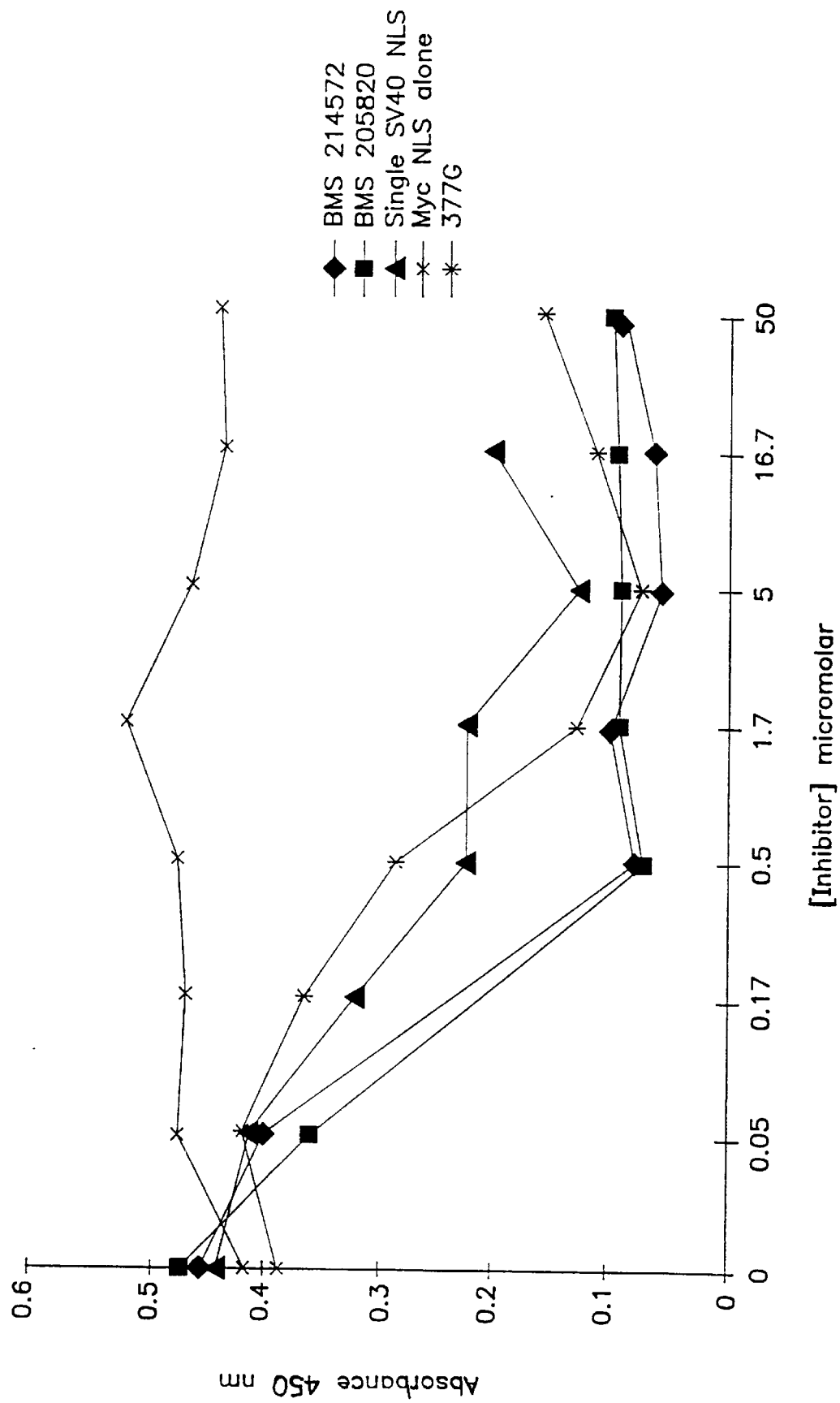
FIG. 14 depicts the effect of BMS-205820, C-MYCMEM (BMS-214572), an SV40 NLS polypeptide containing a single NLS, a c-myc NLS alone, without a translocation sequence (AKRVKL (SEQ ID NO:6)) and a control non-NLS polypeptide, 377G, on lipopolysaccharide (LPS) binding to CD14.

FIG. 14 shows the results of the experiment. Both BMS-205820 and C-MYCMEM were able to bind to LPS and block it from binding CD14. The c-myc NLS did not block binding of LPS to CD 14.

LPS is the causative agent of septic shock. Thus, by blocking binding of LPS to CD 14, the NLS polypeptides described herein may serve to prevent or diminish septic shock in vivo. This result was unexpected. Without being bound by a particular theory, it is possible that positively charged NLS polypeptides bind to negatively charged regions on LPS.

EXAMPLE 18

Ability of BMS-205820 to Treat Asthma

These experiments show that the BMS-205820 polypeptide is efficacious for the treatment of asthma. The BMS-205820 polypeptide was tested in a mouse model of asthma (Renz et al. (1992) J Allergy Clin. Path. 89:1127–1138). Balb/c mice were administered ovalbumin in an alum adjuvant intraperitoneally at various times, as indicated in FIG. 15A. Treatment was followed by nebulization of ovalbumin into the lungs, also as indicated in FIG. 15A. The mice were also treated with 3 mg/kg of the BMS 205820 polypeptide in PBS at the times indicated. Mice were sacrificed at day 18 and the presence of eosinophils assayed. As seen in FIG. 15B, the BMS-205820 polypeptide significantly inhibited the infiltration of eosinophils into the lungs, a measure of the asthmatic state.

EXAMPLE 19

BMS-214572 Affects Mouse Splenic T-Cell Proliferation

Splenic T-cells from BALB/c mice were isolated by glass wool chromatography and treated with either 0.5 or 2.0 μM peptide in 96 well plates for 2 hours followed by activation with either anti-CD3 alone (1.25 mg/ml), PMA alone (1 ng/ml), anti-CD3 plus anti-CD28 (1.25 mg/ml each) or anti-CD28 plus PMA (0.5 mg/ml and 1 ng/ml, respectively). Plates were coated with antibody 24 hours prior to activation. Proliferation was determined after 72 hours by pulsing for 8 hours with [$^3$H]-thymidine, and determining radioactivity incorporated into DNA.

Figure 16:
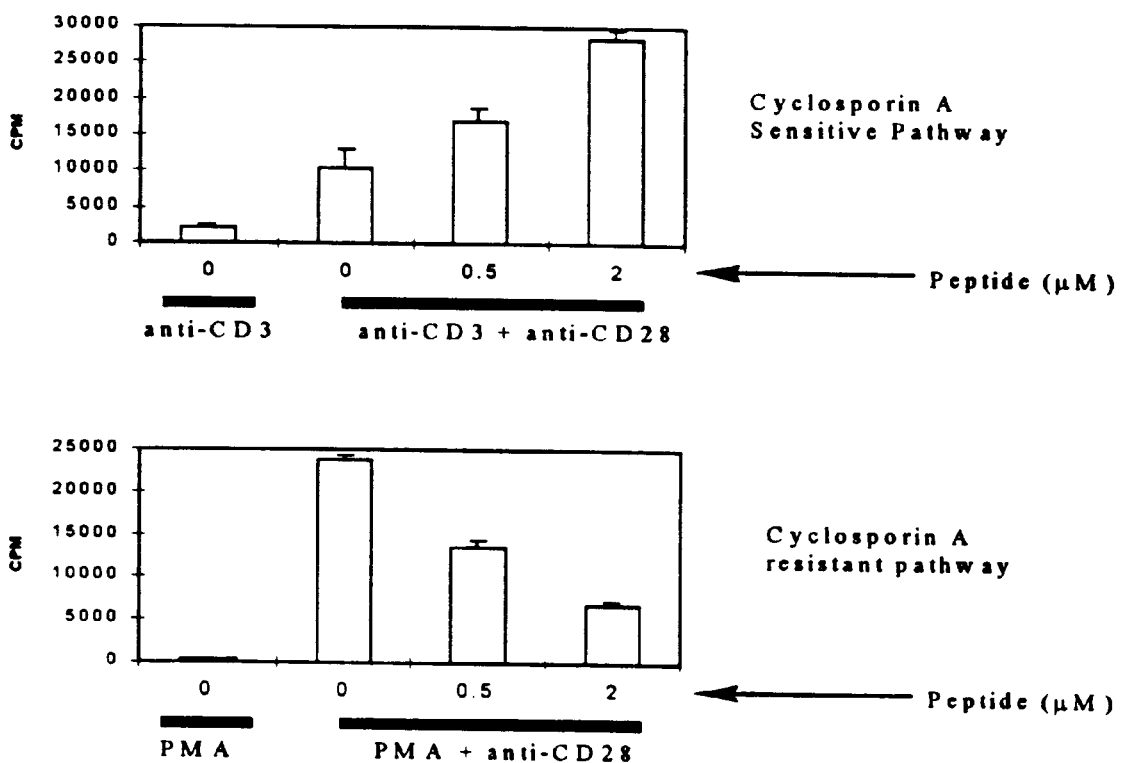
FIG. 16 shows the effect of BMS-214572 on splenic T-cell proliferation.

As shown in FIG. 16, when T cells are stimulated with anti-CD3 +anti-CD28, pretreatment for 2 hours with increasing amounts of peptide results in an augmentation of proliferation. However, when cells are stimulated with PMA+anti-CD28,the peptide effect is reversed and T cell proliferation is inhibited. Both effects are most dramatic when low concentrations of the stimuli are used. One explanation for these disparate effects is that the CD3+CD28 activation pathway is calcium dependent and partially cyclosporin A sensitive, and therefore signals predominantly through a different transcription factor such as NFAT, which is the target of cyclosporin A, as opposed to NF-κB. BMS-214572, by inhibiting NF-κB signaling, may act to indirectly enhance NFAT-mediated T cell activation. In contrast, PMA+anti-CD28 induced proliferation, which is cyclosporin A resistant, may be more NF-κB dependent, and therefore peptide inhibition of T cell activation is more evident under these conditions.

EXAMPLE 20

BMS-205820 Acts In Synergy With Cyclosporin A (CsA) To Inhibit Human Peripheral Blood T-Cell Proliferation Human peripheral blood lymphocytes were isolated and treated with CsA or peptide, or both, for one hour prior to activation on plates coated with antibodies. For the CsA combination study, 1 μM peptide was used. All other experimental details were similar to Example 19.

Figure 17:
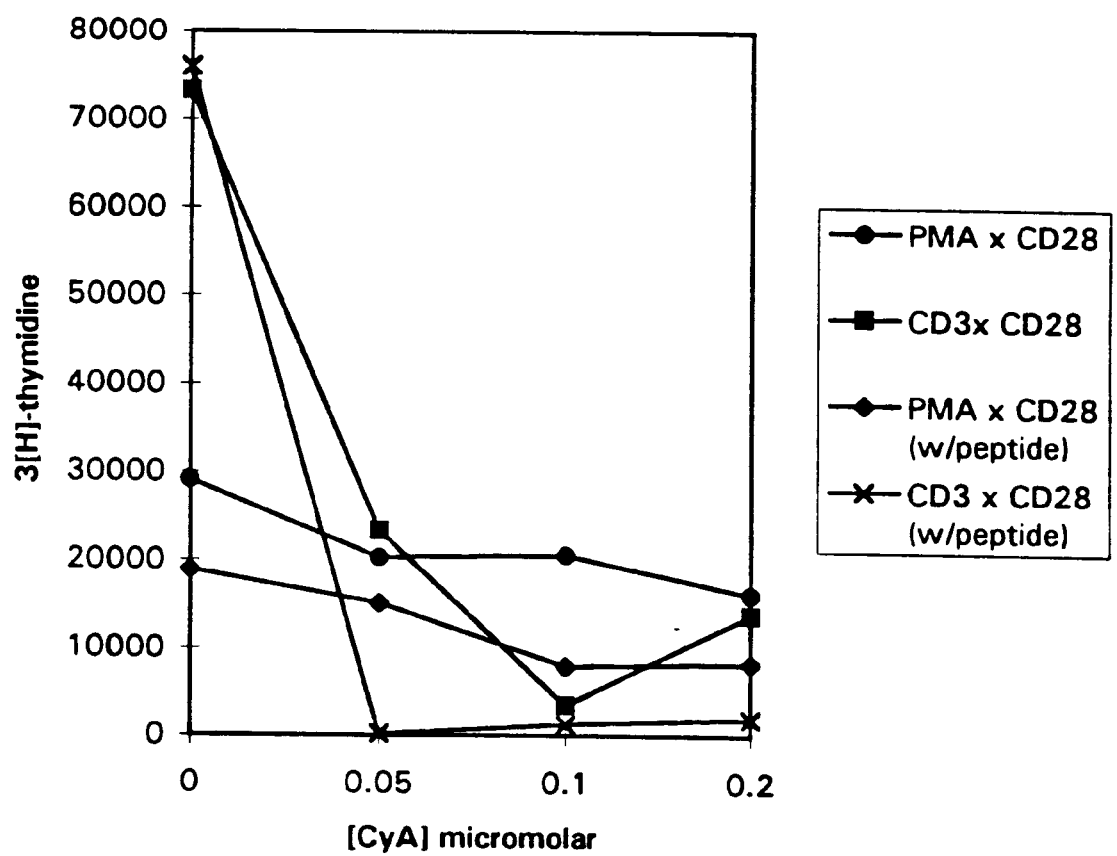
FIG. 17 demonstrates that BMS-205820 acts synergistically with cyclosporin A to inhibit human peripheral blood T-cell proliferation in response to activation with CD3× CD28.

In contrast to the mouse cells in Example 19, the peptide did not stimulate proliferation when the cells were activated with CD3×CD28. There was an inhibition of proliferation when the cells were stimulated through PMA×CD28. CsA also causes a decrease in proliferation in response to the two types of stimuli. The peptide worked additively with CsA to inhibit PMA×CD28 stimulated proliferation and synergistically to inhibit CD3 ×CD28 stimulated proliferation. (FIG. 17)

Thus, compositions comprising immunosuppressants, such as cyclosporin, and polypeptide inhibitors of nuclear translocation of cellular proteins have been disclosed. Although preferred embodiments of the subject invention have been described in some detail, it is understood that obvious variations can be made without departing from the spirit and the scope of the invention as defined by the appended claims.

We claim:

1. A composition comprising at least one isolated polypeptide and at least one immunosuppressant, wherein said at least one isolated polypeptide comprises:

(1) a signal sequence peptide capable of delivering the polypeptide through the cytoplasmic membrane into a cell; and (2) at least one nuclear localization sequence (NLS), and wherein said polypeptide is capable of inhibiting nuclear translocation of a cellular protein.

2. The composition of claim 1, wherein said isolated polypeptide comprises at least two nuclear localization sequences.

3. The composition of claim 2, wherein the signal sequence is interchangeably flanked at its amino- and carboxy-termini by first and second NLSs.

4. The composition of claim 3, wherein the signal sequence peptide is the antennapedia homeodomain signal sequence peptide, the fibroblast growth factor signal sequence peptide, the human immunodeficiency virus (HIV) Tat signal sequence peptide, or the Hsc70 signal sequence peptide.

5. The composition of claim 4, wherein the signal sequence peptide is the antennapedia homeodomain signal sequence peptide.

6. The composition of claim 4, wherein the signal sequence peptide is the fibroblast growth factor signal sequence peptide.

7. The composition of claim 6, wherein the signal sequence peptide comprises the amino acid sequence AAVALLPAVLLALLA (SEQ ID NO:8).

8. The composition of claim 2, wherein said at least two NLSs may be the same or different and are peptides comprising the amino acid sequence selected from the group consisting of PKKKRKV (SEQ ID NO:10), KKKRKVC (SEQ ID NO:11), GKKRSKA (SEQ ID NO:12), KRPRP (SEQ ID NO:13), GNKAKRQRST (SEQ ID NO:14), GGAAKRVKLD (SEQ ID NO:15), SALIKKKKKMAP (SEQ ID NO:16), RKLKKLGN (SEQ ID NO:17), PQPKKKP (SEQ ID NO:18), ASKSRKRKL (SEQ ID NO:19), KKKYK (SEQ ID NO:20), KKKYKC (SEQ ID NO:21), KSKKK (SEQ ID NO:22), KRVKLC (SEQ ID NO:23), and AKRVKL (SEQ ID NO:6).

9. The composition of claim 3, wherein said at least two NLSs may be the same or different and are peptides comprising the amino acid sequence selected from the group consisting of PKKKRKV (SEQ ID NO:10), KKKRKVC (SEQ ID NO:11), GKKRSKA (SEQ ID NO:12), KRPRP (SEQ ID NO:13), GNKAKRQRST (SEQ ID NO:14), GGAAKRVKLD (SEQ ID NO:15), SALIKKKKKMAP (SEQ ID NO:16), RKLKKLGN (SEQ ID NO:17), PQPKKKP (SEQ ID NO:18), ASKSRKRKL (SEQ ID NO:19), KKKYK (SEQ ID NO:20), KKKYKC (SEQ ID NO:21), KSKKK (SEQ ID NO:22), KRVKLC (SEQ ID NO:23), and AKRVKL (SEQ ID NO:6).

10. The composition of claim 9, wherein each of said at least two NLSs comprise the amino acid sequence PKKKRKV (SEQ ID NO:10).

11. The composition of claim 10, wherein said isolated polypeptide comprises the amino acid sequence PKKKRKVAAVALLPAVLLALLAPKKKRKV (SEQ ID NO:24).

12. The composition of claim 1, wherein said at least one immunosuppressant is selected from the group consisting of cyclosporin, mycophenolate mofetil, steroids, rapamycin, and FK506.

13. The composition of claim 12, wherein said at least one immunosuppressant comprises cyclosporin.

14. The composition of claim 11, wherein said at least one immunosuppressant is selected from the group consisting of cyclosporin, mycophenolate mofetil, steroids, rapamycin and FK506.

15. The composition of claim 14, wherein said at least one immunosuppressant comprises cyclosporin.

16. The composition of claim 1, wherein said isolated polypeptide comprises the amino acid sequence PKKKRKVAAVALLPAVLLALLAPKKKRKV (SEQ ID NO:24) and said immunosuppressant comprises cyclosporin.

17. The composition of claim 11 wherein said isolated polypeptide comprises D-amino acids.

* * * * *

```
SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
         (A) LENGTH: 30 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Pro Lys Lys Lys Arg Lys Val Ala Ala Val Ala Leu Leu Pro Ala Val
1               5                  10                  15

Leu Leu Ala Leu Leu Ala Pro Lys Lys Lys Arg Lys Val Cys
            20                  25                  30

(2) INFORMATION FOR SEQ ID NO:2:

(i) SEQUENCE CHARACTERISTICS:
         (A) LENGTH: 26 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Lys Lys Lys Tyr Lys Ala Ala Val Ala Leu Leu Pro Ala Val Leu Leu
1               5                  10                  15

Ala Leu Leu Ala Lys Lys Lys Tyr Lys Cys
            20                  25

(2) INFORMATION FOR SEQ ID NO:3:

(i) SEQUENCE CHARACTERISTICS:
         (A) LENGTH: 27 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:3:

Ala Lys Arg Val Lys Leu Ala Ala Val Ala Leu Leu Pro Ala Val Leu
1               5                  10                  15

Leu Ala Leu Leu Ala Lys Arg Val Lys Leu Cys
            20                  25

(2) INFORMATION FOR SEQ ID NO:4:
```

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:4:

Ala Ala Val Ala Leu Leu Pro Ala Val Leu Leu Ala Leu Leu Ala Pro
1               5                   10                  15

(2) INFORMATION FOR SEQ ID NO:5:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Ala Lys Arg Val Lys Leu
1               5

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Arg Gln Ile Lys Ile Trp Phe Gln Asn Arg Arg Met Lys Trp Lys Lys
1               5                   10                  15

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ala Ala Val Ala Leu Leu Pro Ala Val Leu Leu Ala Leu Leu Ala
1               5                   10                  15

(2) INFORMATION FOR SEQ ID NO:9:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Cys Phe Ile Thr Lys Ala Leu Gly Ile Ser Tyr Gly Arg Lys Lys Arg
1               5                  10                  15

Arg Gln Arg Arg Arg Pro Pro Gln Gly Ser Gln Thr His
            20                  25
```

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Pro Lys Lys Lys Arg Lys Val
1               5
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Lys Lys Lys Arg Lys Val Cys
1               5
```

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Gly Lys Lys Arg Ser Lys Ala
1               5
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Lys Arg Pro Arg Pro
1               5

(2) INFORMATION FOR SEQ ID NO:14:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gly Asn Lys Ala Lys Arg Gln Arg Ser Thr
1               5                   10

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Gly Gly Ala Ala Lys Arg Val Lys Leu Asp
1               5                   10

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ser Ala Leu Ile Lys Lys Lys Lys Lys Met Ala Pro
1               5                   10

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Arg Lys Leu Lys Lys Leu Gly Asn
1               5

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Pro Gln Pro Lys Lys Pro
1               5
```

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Ala Ser Lys Ser Arg Lys Arg Lys Leu
1               5
```

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Lys Lys Lys Tyr Lys
1               5
```

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Lys Lys Lys Tyr Lys Cys
1               5
```

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Lys Ser Lys Lys Lys
1               5
```

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

-continued

```
Lys Arg Val Lys Leu Cys
1               5
```

(2) INFORMATION FOR SEQ ID NO:24:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Pro Lys Lys Arg Lys Val Ala Ala Val Ala Leu Leu Pro Ala Val
1               5                  10                  15

Leu Leu Ala Leu Leu Ala Pro Lys Lys Arg Lys Val
            20                  25
```